US008198298B2

(12) United States Patent
Salom et al.

(10) Patent No.: US 8,198,298 B2
(45) Date of Patent: Jun. 12, 2012

(54) PYRROLO[2,3-B]PYRIDINE DERIVATIVES ACTIVE AS KINASE INHIBITORS

(75) Inventors: Barbara Salom, Milan (IT); Matteo D'Anello, Milanese (IT); Maria Gabriella Brasca, Milan (IT); Patrizia Giordano, Cuneo (IT); Katia Martina, Novara I (IT); Dania Tesei, Ancona (IT); Frederick Arthur Brookfield, Oxon (GB); William John Trigg, Oxon (GB); Edward Andrew Boyd, Berkshire (GB); Jonathan Anthony Larard, York (GB)

(73) Assignee: Pfizer Italia S.r.l., Rome (IT)

( * ) Notice: Subject to any disclaimer, the term of this patent is extended or adjusted under 35 U.S.C. 154(b) by 54 days.

(21) Appl. No.: 13/026,789

(22) Filed: Feb. 14, 2011

(65) Prior Publication Data

US 2011/0136857 A1   Jun. 9, 2011

Related U.S. Application Data

(62) Division of application No. 11/020,794, filed on Dec. 23, 2004, now Pat. No. 7,888,508.

(30) Foreign Application Priority Data

Dec. 24, 2003 (GB) .................................. 0330042.3

(51) Int. Cl.
*A61K 31/44* (2006.01)
(52) U.S. Cl. ...................................................... 514/300
(58) Field of Classification Search .................... 514/300
See application file for complete search history.

(56) References Cited

U.S. PATENT DOCUMENTS

| 3,320,268 | A | 5/1967 | Tusng-Ying Shen et al. |
| 5,663,346 | A | 9/1997 | Buzzetti et al. |
| 6,476,034 | B2 | 11/2002 | Wang et al. |
| 6,632,819 | B1 | 10/2003 | Wang et al. |
| 7,888,508 | B2 * | 2/2011 | Salom et al. ................. 546/113 |

FOREIGN PATENT DOCUMENTS

| WO | WO 95/28400 | 10/1995 |
| WO | WO 96/11929 | 4/1996 |
| WO | WO 97/03069 | 1/1997 |
| WO | WO 98/50364 | 11/1998 |
| WO | WO 99/32111 | 7/1999 |
| WO | WO 99/37637 | 7/1999 |
| WO | WO 99/58496 | 11/1999 |
| WO | WO 00/21950 | 4/2000 |
| WO | WO 00/21951 | 4/2000 |
| WO | WO 00/24717 | 5/2000 |
| WO | WO 00/71537 | 11/2000 |
| WO | WO 01/01986 | 1/2001 |
| WO | WO 01/58869 | 8/2001 |
| WO | WO 01/98299 | 12/2001 |
| WO | WO 03/082868 | 10/2003 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Cohen P., "The Development and Therapeutic Potential of Protein Kinase Inhibitors", *Current Opinion in Chemical Biology* 3:459-465 (1999).
Hosoi T. et al., "Evidence for CdkS as a Major Activity Phosphorylating Tau Protein in Porcine Brain Extract", *J. Biochem.* 117(4):741-749 (1995).
Schneller S.W. et al., "Synthesis of 4-Amino-1H-Pyrrolo[2,3-b]Pyridine (1,7-Dideazaadenine) and 1H-Pyrrolo[2,3-b]Pyridin-4-ol (1,7-Dideazahypoxanthine)", *Journal of Organic Chemistry* 45(20):4045-4048 (1980), Chemical Abstracts C.A. 93:168162.
Brodrick A. et al., "1H-Pyrrolo[2,3-b]Pyridines. Part III. A Novel Synthetic Route from 1-Substituted 2-Aminopyrroles", *J.C.S. Perkin Trans. I: Organic and Bio-Organic Chemistry* 19:1910-1913 (1975).
Levacher V. et al., "One Pot Synthesis of Pyrrolo[2,3-b]Pyridine Derivatives", *Synthetic Communications* 24(19):2697-2705 (1994).
Allegretti M. et al., "A Practical Synthesis of 7-Azaindolylcarboxy-Endo-Tropanamide (DF 1012)", *Organic Process Research & Development* 7(2):209-213 (2003).
Huang X. et al., "Expanding Pd-Catalyzed C-N Bond-Forming Processes: The First Amidation of Aryl Sulfonates, Aqueous Amination, and Complementarity with Cu-Catalyzed Reactions", *J. Am. Chem. Soc.* 125(22):6653-6655 (2003).
Ali M.H. et al., "An Improved Method for the Palladium-Catalyzed Amination of Aryl Iodides", *J. Org. Chem.* 66(8):2560-2565 (2001).
Kuwano R. et al., "Aqueous Hydroxide as a Base for Palladium-Catalyzed Amination of Aryl Chlorides and Bromides", *J. Org. Chem.* 67(18):6479-6486 (2002).
Ferreira P.M.T. et al., "Synthesis of β-Substituted Alanines via Michael Addition of Nucleophiles to Dehydroalanine Derivatives", *J. Chem. Soc., Perkin Trans. I*, 19:3317-3324 (2000).
Rolland-Fulcrand V. et al., "Efficient Chemoenzymatic Synthesis of Enantiomerically Pure β-Heterocyclic Amino Acid Derivatives", *Tetrahedron Asymmetry* 11:4719-4724 (2000).
Fivush A.M. et al., "AMEBA: An Acid Sensitive Aldehyde Resin for Solid Phase Synthesis", *Tetrahedron Letters* 38(41):7151-7154 (1997).
Jensen K.J. et al., "Backbone Amide Linker (BAL) Strategy for Solid-Phase Synthesis of C-Terminal-Modified and Cyclic Peptides", *J. Am. Chem. Soc.* 120(22):5441-5452 (1998).

(Continued)

*Primary Examiner* — Andrew D Kosar
*Assistant Examiner* — Raymond Covington
(74) *Attorney, Agent, or Firm* — Scully, Scott, Murphy & Presser, P.C.

(57) ABSTRACT

Compounds which are pyrrolo[2,3-b]pyridine derivatives or pharmaceutically acceptable salts thereof, their preparation process and pharmaceutical compositions comprising them are disclosed; these compounds are useful in the treatment of diseases caused by and/or associated with an altered protein kinase activity such as cancer, cell proliferative disorders, Alzheimer's disease, viral infections, auto-immune diseases and neurodegenerative disorders; also disclosed is a process under SPS conditions for preparing the compounds of the invention and chemical libraries comprising a plurality of them.

14 Claims, No Drawings

OTHER PUBLICATIONS

Alsina J. et al., "Solid-Phase Synthesis with Tris(alkoxy)benzyl Backbone Amide Linkage (BAL)", *Chem. Eur. J.* 5(10):2787-2795 (1999).

Palmer B.D. et al., "Structure-Activity Relationships for 5-Substituted 1-Phenylbenzimidazoles as Selective Inhibitors of the Platelet-Derived Growth Factor Receptor", *J. Med. Chem.* 42(13):2373-2382 (1999).

Lackey K. et al., "The Discovery of Potent cRafl Kinase Inhibitors", *Bioorganic & Medicinal Chemistry Letters* 10:223-226 (2000).

Office Action dated Aug. 22, 2007 U.S. Appl. No. 11/020,794.
Office Action dated Apr. 14, 2008 U.S. Appl. No. 11/020,794.
Office Action dated Oct. 16, 2008 U.S. Appl. No. 11/020,794.
Final Office Action dated Jul. 8, 2009 U.S. Appl. No. 11/020,794.
Office Action dated Mar. 29, 2010 U.S. Appl. No. 11/020,794.

* cited by examiner

US 8,198,298 B2

PYRROLO[2,3-B]PYRIDINE DERIVATIVES ACTIVE AS KINASE INHIBITORS

CROSS REFERENCE TO RELATED APPLICATIONS

The present application is a divisional of copending application Ser. No. 11/020,794 filed Dec. 23, 2004, which claims benefit of British Patent Application No. 0330042.3 filed Dec. 24, 2003, the entire contents of which are incorporated herein by reference.

BACKGROUND OF THE INVENTION

1. Field of the Invention

The present invention relates to pyrrolo[2,3-b]pyridine derivatives active as kinase inhibitors and, more in particular, it relates to pyrrolo[2,3-b]pyridine derivatives further substituted in position 5, to a process for their preparation, to combinatorial libraries thereof, to pharmaceutical compositions comprising them and to their use as therapeutic agents, particularly in the treatment of diseases linked to disregulated protein kinases.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

SUMMARY OF THE INVENTION

It is an object of the invention to provide compounds that are useful in therapy as agents against a host of diseases caused by and/or associated to a disregulated protein kinase activity.

It is another object to provide compounds that are endowed with protein kinase inhibiting activity.

The present inventors have now discovered that some pyrrolo[2,3-b]pyridine derivatives are endowed with protein kinase inhibiting activity and may be thus useful in therapy in the treatment of diseases associated with disregulated protein kinases.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumours of lymphoid lineage, including leukemia, acute lymphocite leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumours of myeloid lineage, including acute and chronic myelogenous leukemias, myelodysplastic syndrome and promyelocytic leukemia; tumours of mesenchymal origin, including fibrosarcoma and rhabdomyosarcoma; tumours of the central and peripheral nervous system, including astrocytoma, neuroblastoma, glioma and schwannomas; other tumours, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these pyrrolo[2,3-b]pyridine compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention are, in addition, useful in the treatment of Alzheimer's disease, as suggested by the fact that cdk5 is involved in the phosphorylation of tau protein (J. Biochem., 117, 741-749, 1995).

The compounds of this invention, as modulators of apoptosis, are useful in the treatment of cancer, viral infections, prevention of AIDS development in HIV-infected individuals, autoimmune diseases and neurodegenerative disorders.

The compounds of this invention are useful in inhibiting tumour angiogenesis and metastasis, as well as in the treatment of organ transplant rejection and host versus graft disease.

The compounds of the invention also act as inhibitor of other protein kinases, e.g., cyclin-dependent kinases (cdk) such as cdk2 and cdk5, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, PI3K, weel kinase, Src, Abl, Akt, MAPK, ILK, MK-2, IKK-2, Cdc7, Nek, and thus be effective in the treatment of diseases associated with other protein kinases.

The compounds of the invention are also useful in the treatment and prevention of radiotherapy-induced or chemotherapy-induced alopecia.

DETAILED DESCRIPTION OF THE INVENTION

Pyrrolo-pyridine derivatives are widely known in the art. As an example, the compound 3-carboxamido-pyrrolo[2,3-b]pyridine is reported as synthetic intermediate in Chemical Abstracts C.A. 93 (1980):168162.

Some other 3-carboxamido derivatives of pyrrolo-pyridine further N-substituted by indolyl groups are disclosed as 5-HT2C/2B antagonists (see WO 96/11929); the above 3-carboxamido derivatives further substituted by N-(isoquinolyl-ethyl-cyclohexyl) groups are disclosed as antipsychotic agents (see WO 00/24717; WO 00/21951; WO 00/21950; WO 98/50364); 3-carboxamido-pyrrolo-pyridine compounds N-substituted by azabicyclo rings are also disclosed as synthetic intermediates in the preparation of tropyl derivatives, possessing antitussive properties.

Moreover, 3-hydrazido pyrrolo-pyridine derivatives are disclosed as synthetic intermediates for preparing more complex protein kinase inhibitors, as reported in WO 00/71537.

7-Azaindoles as inhibitors of C-JUN N-terminal kinases and thus useful in the treatment of neurodegenerative disorders are also disclosed in WO 03/082868. However, none of the pyrrolo-pyridine derivatives of the prior art resulted to bear an additional amino group, optionally further functionalised, in position 5 of the pyrrolo-pyridine skeleton.

Broad general formula pyrrolo[2,3-b]pyridine compounds endowed with therapeutic activity, also including protein kinase inhibitory activity, are also disclosed in WO 00/71537; WO 01/01986; WO 01/58869; WO 99/32111; WO 99/37637; WO 97/03069; WO 99/58496 and WO 95/28400.

3-Alkenyl-pyrrolo[2,3-b]pyridine derivatives as protein kinase inhibitors are also disclosed in WO 01/98299 in the name of the Applicant itself.

Accordingly, the present invention provides a method for treating diseases caused by and/or associated with an altered protein kinase activity, by administering to a mammal in need thereof an effective amount of a compound represented by formula (I)

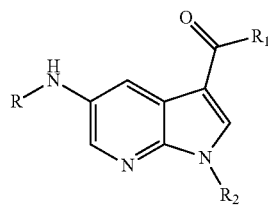

(I)

wherein

R is selected from the group consisting of —$R^a$, —$COR^a$, —$CONR^aR^b$, —$SO_2R^a$ or —$COOR^a$;

$R_1$ is a group —$NR^cR^d$ or —$OR^c$;

wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional heteroatom or heteroatomic group selected from S, O, N or NH;

$R_2$ is a group, optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl; or isomers, tautomers, carriers, metabolites, prodrugs, and pharmaceutically acceptable salts thereof.

In a preferred embodiment of the method described above, the disease caused by and/or associated with an altered protein kinase activity is selected from the group consisting of cancer, cell proliferative disorders, Alzheimer's disease, viral infections, autoimmune diseases and neurodegenerative disorders.

Specific types of cancer that may be treated include carcinoma, squamous cell carcinoma, hematopoietic tumours of myeloid or lymphoid lineage, tumours of mesenchymal origin, tumours of the central and peripheral nervous system, melanoma, seminoma, teratocarcinoma, osteosarcoma, xeroderma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

The present invention further provides a compound represented by formula (I)

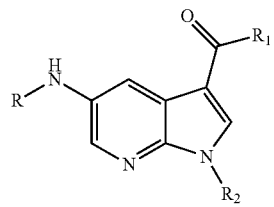

(I)

wherein

R is selected from the group consisting of —$R^a$, —$COR^a$, —$CONR^aR^b$, —$SO_2R^a$ or —$COOR^a$;

$R_1$ is a group —$NR^cR^d$ or —$OR^c$;

wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional heteroatom or heteroatomic group selected from S, O, N or NH;

$R_2$ is a group, optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl; or isomers, tautomers, carriers, metabolites, prodrugs, and pharmaceutically acceptable salts thereof.

Unless otherwise specified, when referring to the compounds of formula (I) per se as well as to any pharmaceutical composition thereof or to any therapeutic method of treatment comprising them, the present invention includes all of the hydrates, solvates, complexes, metabolites and prodrugs of the compounds of this invention. Prodrugs are any covalently bonded compounds, which release the active parent drug according to formula (I) in vivo.

If a chiral center or another form of an isomeric center is present in a compound of the present invention, all forms of such isomer or isomers, including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone. In cases wherein compounds may exist in tautomeric forms, such as keto-enol tautomers, each tautomeric form is contemplated as being included within this invention whether existing in equilibrium or predominantly in one form.

In the present description, unless otherwise indicated, with the term straight or branched $C_1$-$C_6$ alkyl we intend any group such as, for instance, methyl, ethyl, n-propyl, isopropyl, n-butyl, isobutyl, sec-butyl, tert-butyl, n-pentyl, n-hexyl, and the like.

With the term straight or branched $C_2$-$C_6$ alkenyl or alkynyl we intend any of the unsaturated alkenyl or alkynyl groups with from 2 to 6 carbon atoms for instance including vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term $C_3$-$C_6$ cycloalkyl we intend any 3 to 6 membered carbocyclic ring such as, for instance, cyclopropyl, cyclobutyl, cyclopentyl and cyclohexyl.

Unless otherwise specified, with the term aryl we intend a mono- or bi-cyclic, either carbocycle as well as heterocycle, with 1 or 2 ring moieties either fused or linked to each other by single bonds, wherein at least one of the carbocyclic or heterocyclic rings is aromatic; but it also includes 1 or 2 ring moieties, wherein all of the rings are aromatic. Unless otherwise specified, the said heterocycle is a 4 to 7 membered ring with from 1 to 3 ring heteroatoms or heteroatomic groups selected among N, NH, O and S.

Non limiting examples of aryl groups of the invention are, for instance, phenyl, indanyl, biphenyl, α- or β-naphthyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, quinolinyl, isoquinolinyl, quinoxalinyl, benzofurazanyl, 1,2,3-triazolyl, 1-phenyl-1,2,3-triazolyl, and the like.

With the term heterocycle (e.g. heterocyclyl) or heterocyclic group we also intend a 4 to 7 membered heterocycle, hence encompassing aromatic heterocyclic groups also known as heteroaryl groups and presently encompassed by the term aryl, as well as heterocycles being saturated or partially unsaturated with from 1 to 3 ring heteroatoms or heteroatomic groups selected among N, NH, O and S.

Examples of these 4 to 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

When referring to the compounds of formula (I) wherein R is a group —CONR$^a$R$^b$ and/or R$_1$ is a group —NR$^c$R$^d$ and R$^a$ and R$^b$ and/or R$^c$ and R$^d$ are taken together with the nitrogen atom to which they are bonded, they may also form an optionally substituted 4 to 7 membered heterocycle optionally containing one additional ring heteroatom or heteroatomic group among S, O, N or NH.

According to the meanings provided to R$^a$, R$^b$, R$^c$, R$^d$ and R$_2$, any of the above groups may be further optionally substituted in any of their free positions by one or more groups, for instance 1 to 6 groups, selected from: halogen, nitro, oxo groups (=O), carboxy, cyano, alkyl, polyfluorinated alkyl, alkenyl, alkynyl, cycloalkyl, cycloalkenyl; aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups. In the present description, unless otherwise specified, with the term halogen atom we intend a fluorine, chlorine, bromine or iodine atom.

With the term polyfluorinated alkyl or alkoxy we intend a straight or branched C$_1$-C$_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the terms heterocyclyl-alkyl and cycloalkyl-alkyl stand for a straight or branched alkyl group being further substituted by a heterocyclic or cycloalkyl group, respectively, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A first class of preferred compounds of the invention is represented by the derivatives of formula (I) wherein R$_1$ is a group —NR$^c$R$^d$ and R$^c$ and R$^d$ are both hydrogen atoms or one of them is a hydrogen atom and the remaining one of R$^c$ or R$^d$ is a straight or branched alkyl or alkenyl group or it is an optionally substituted aryl or arylalkyl group; and R and R$_2$ are as above defined.

Another class of preferred compounds of the invention is represented by the derivatives of formula (I) wherein R is either a group R$^a$ with R$^a$ as a hydrogen atom or a group —SO$_2$R$^a$ with R$^a$ as a straight or branched alkyl or optionally substituted aryl or arylalkyl group; and R$_1$ and R$_2$ are as above defined.

Another class of preferred compounds of the invention is represented by the derivatives of formula (I) wherein R is a group —COR$^a$ with R$^a$ as a straight or branched alkyl, cycloalkyl or optionally substituted aryl or arylalkyl group; and R$_1$ and R$_2$ are as above defined.

Another class of preferred compounds of the invention is represented by the derivatives of formula (I) wherein R is a group —CONR$^a$R$^b$ with one of R$^a$ and R$^b$ as a hydrogen atom and the other of R$^a$ and R$^b$ as a straight or branched alkyl, optionally substituted aryl or arylalkyl group; and R$_1$ and R$_2$ are as above defined.

Another class of preferred compounds of the invention is represented by the derivatives of formula (I) wherein R is a group —CONR$^a$R$^b$ and wherein R$^a$ and R$^b$ form, together with the nitrogen atom to which they are bonded, an optionally substituted 6 membered heterocyclic ring; and $R_1$ and $R_2$ are as above defined.

Another class of preferred compounds of the invention is represented by the derivatives of formula (I) wherein $R_2$ is a straight or branched alkyl or alkenyl group or it is a cycloalkyl, cycloalkyl-alkyl or an optionally substituted aryl or arylalkyl group; and R and $R_1$ are as above defined.

Preferably, within the above classes, R, $R_1$ and $R_2$ are selected, each independently, according to the meanings reported in tables I, II and III of the experimental section.

For a reference to any specific compound of formula (I) of the invention, optionally in the form of pharmaceutically acceptable salts, see the experimental section.

As set forth above, it is a further object of the present invention a process for preparing the compounds of formula (I).

Therefore, the compounds of formula (I) and the pharmaceutically acceptable salts thereof may be obtained by a process comprising:

a) reacting a formyl-succinonitrile alkaline salt derivative below

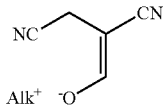

wherein $Alk^+$ stands for $Na^+$ or $K^+$, with a suitable amine of formula (II)

     (II)

wherein $R_2$ is as above defined, under basic conditions, so as to obtain the compound of formula (III)

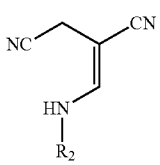     (III)

b) reacting the compound of formula (III) with a base so as to obtain a pyrrole derivative of formula (IV)

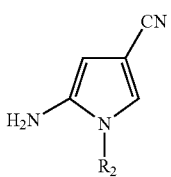     (IV)

c) reacting the compound of formula (IV) with sodium nitromalonaldehyde so as to obtain the compound of formula (V)

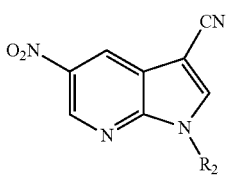     (V)

d) reacting the compound of formula (V) under acidic conditions and in the presence of a suitable alcohol of formula (VI)

     (VI)

wherein R is a straight or branched lower alkyl group, so as to obtain the compound of formula (VII)

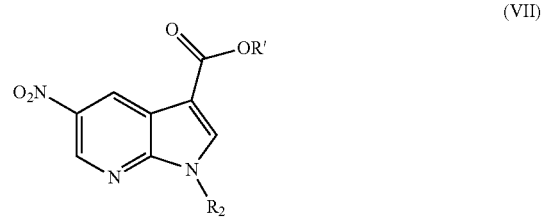     (VII)

e) reacting the compound of formula (VII) with tin(II) chloride so as to obtain a compound of formula (I)

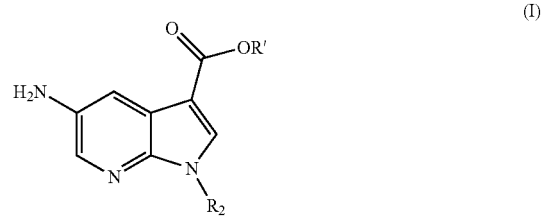     (I)

wherein $R_2$ and R' are as above defined and, optionally, reacting it according to any one of the alternative steps (f.1), (f.2), (f.3) or (f.4)

f.1) with any one of the compounds of formula (VIII), (IX), (X) or (XI)

$R^a COZ$     (VIII);

$R^a NCO$     (IX);

$R^a SO_2 Z$     (X);

$R^a OCOZ$     (XI)

wherein $R^a$ is as above defined and Z is a halogen atom, so as to obtain the compound of formula (I)

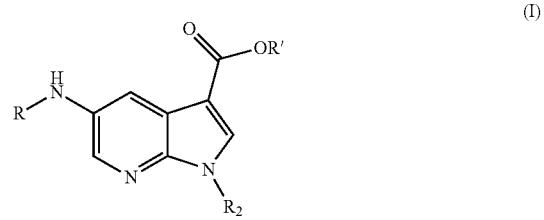     (I)

wherein R' is as above defined and R is a group $—COR^a$, $—CONHR^a$, $—SO_2R^a$ or $—COOR^a$, respectively; or f.2) with a suitable amine of formula (XII) in the presence of triphosgene or of a suitable chloroformate $HNR^a R^b$     (XII)

so as to obtain the above compound of formula (I) wherein R is a group $—CONR^a R^b$; or (f.3) with a suitable aldehyde or ketone derivative of formula (XIII) under reductive operative conditions $R^a—CO—R^a$     (XIII)

wherein each $R^a$ is the same or different as formerly defined, so as to obtain the above compound of formula (I) wherein R is a group $—CH(R^a)R^a$; or (f.4) with an aromatic iodide or bromide of formula (XIV)

$R^a—X$     (XIV)

wherein X represents a iodine or bromine atom and $R^a$ represents a carbocyclic or heterocyclic aryl group, in the presence of a suitable palladium catalyst and of a ligand, so as to obtain a compound of formula (I) wherein R is $R^a$ and this latter has the above reported meanings; and, optionally g) converting the compound of formula (I) being obtained according to any one of steps (e), (f.1), (f.2), (f.3) or (f.4) into another compound of formula (I) and/or into a pharmaceutically acceptable salt thereof.

The above process is an analogy process which can be carried out according to well-known methods.

According to step (a) of the process, the formyl-succinonitrile alkaline salt is reacted with a suitable amine of formula (II) wherein $R_2$ is as defined in formula (I), so as to get the corresponding compound of formula (III). Preferably, the reaction occurs by starting from formyl-succinonitrile potassium salt.

The reaction is carried out under basic conditions, for instance in the presence of sodium methylate, sodium ethylate, sodium hydride, potassium tert-butoxide and the like, in a suitable solvent such as toluene or tetrahydrofuran, at a temperature ranging from room temperature to reflux. For a general reference to the operative conditions leading to the preparation of the compound of formula (III) see, for instance, J.C.S. Perkin Trans. I: Organic and Bio-Organic Chemistry (1972-1999), (1975), (19), 1910-13; Synthetic Communication, 24(19), 2697-2705 (1994); and Org. Proc. Res. Dev., 7 (2), 209-213, 2003.

According to step (b) of the process, the compound of formula (III) is further reacted under basic conditions without the need of being isolated and further purified.

Preferably, the reaction is carried out with an alkali hydroxide, for instance an excess of sodium or potassium hydroxide, in a suitable solvent like a lower alcohol, for instance ethanol (for a general reference to the above reaction conditions see, as an example, the aforementioned journals).

According to step (c) of the process, the compound of formula (IV) is reacted with sodium nitromalonaldehyde so as to get the formation of the azaindole bicyclic ring structure of formula (V). The reaction is carried out in the presence of a suitable solvent, for instance a lower alcohol, under acidic conditions, for instance in the presence of a mineral acid, preferably hydrochloric acid.

With the term lower alcohol herewith intended is any straight or branched alcohol with from 1 to 4 carbon atom; preferably, the reaction is carried out in the presence of n-propanol.

According to step (d) of the process, the compound of formula (V) is converted into the corresponding carboxyester derivative of formula (VII) by working according to conventional techniques, that is in the presence of a suitable lower alcohol of formula (VI). Typically, by employing a large excess of the same alcohol, it may act both as a reactant as well as solvent medium. Preferably, the reaction is carried out with n-propanol so as to lead to the compound of formula (VII) wherein R' just represents n-propyl.

According to step (e) of the process, the nitro group of the compound of formula (VII) is reduced to the corresponding amino derivative. The reduction is preferably carried out in the presence of tin(II) chloride in N-methylpyrrolidone (NMP) according to well-known methods. Clearly, any of the several methods known in the art to reduce nitro groups to amino groups, for instance comprising catalytic hydrogenation, may be successfully employed as well.

From the above, it is clear to the skilled man that the above reaction of step (e) allows to obtain a compound of formula (I) wherein R is a hydrogen atom, $R_1$ is a group $—OR^c$ wherein $R^c$ is just the alkyl group R' being introduced through step (d) of the process, e.g. n-propyl, and $R_2$ is as set forth in formula (I).

The compound of formula (I) thus obtained can then be converted into a variety of derivatives of formula (I) by working as described in any one of steps from (f.1) to (f.4) of the process, according to well-known methods.

Typically, the compound of formula (I) of step (e) bearing an amino group in position 5 may be reacted: with a compound of formula (VIII) so as to get the corresponding carboxamido derivative wherein R is $—COR^a$ and $R^a$ is as above defined; with a compound of formula (IX) so as to get the corresponding ureido derivative wherein R is $—CONHR^a$ and $R^a$ is as above defined; with a compound of formula (X) so as to get a sulfonamido derivative wherein R is $—SO_2R^a$ and $R^a$ is as above defined; with a compound of formula (XI) so as to get a carbamate derivative wherein R is $—COOR^a$ and $R^a$ is as above defined; with a compound of formula (XII) and triphosgene or a suitable chloroformate so as to get an ureido derivative wherein R is $—CONR^aR^b$ and $R^a$ and $R^b$ are as above defined; with a compound of formula (XIII) under reductive operative conditions so as to get a derivative wherein R is $—CH(R^a)R^a$ and each $R^a$, the same or different and independently from each other, is as above defined.

Any one of the above reactions is carried out according to conventional methods normally used in the preparation of functionalized amino derivatives, by starting from the corresponding amine.

Within the compounds of formula (VIII), (X) or (XII) of step (f.1), Z represents a halogen atom and, even more preferably, a chlorine atom.

In this respect, the compound of formula (I) of step (e) is dissolved in a suitable solvent such as dichloromethane, dimethylformamide, tetrahydrofuran, dioxane or the like, and a suitable base such as triethylamine, diisopropylethylamine or sodium carbonate is added therein. The compound of general formula (VIII), (X) or (XI) is then added and the mixture stirred for a time of about 2 hours to about 15 hours, at a temperature ranging from about 20° C. to about 80° C. When using an isocyanate of general formula (IX), the reaction conditions are the same as above reported except that the base may not be required. In all of these reactions, a suitable catalyst such as dimethylamino pyridine may be optionally used.

According to step (f.2) of the process, the compound of formula (I) obtained in step (e) may be reacted with an amino derivative of formula (XII) in the presence of triphosgene or of a suitable chloroformate such as, for instance, 4-nitrophenylchloroformate.

The reaction is carried out in a suitable solvent such as a halogenated hydrocarbon, preferably dichloromethane, in the presence of a base such as, for instance, diisopropylethylamine or triethylamine and by working at room temperature.

According to step (f.3) of the process, the compound of formula (I) of step (e) is reacted, under reductive conditions, with an aldehyde or ketone derivative of formula (XIII) so as to obtain the corresponding compound of formula (I) wherein R is as above defined. From the above, it is clear to the skilled man that by employing an aldehyde derivative of formula (XIII) wherein one of the two $R^a$ is a hydrogen atom, the corresponding derivative wherein R is $—CH_2R^a$ may be obtained. Likewise, by employing a ketone derivative, compounds having R as $—CH(R^a)R^a$ may be obtained, wherein each $R^a$ is, independently from each other, as set forth above but other than hydrogen.

According to step (f.4) of the process, the compound of formula (I) of step (e) is converted into the corresponding arylated derivative of formula (I) wherein R is $R^a$ and $R^a$ is an aryl group, hence comprehensive of carbocyclic or heterocyclic aromatic groups.

The reaction is carried out according to known methods, with any suitable aryl iodide or bromide of formula (XIV) in the presence of a suitable catalyst, for instance a palladium catalyst like palladium acetate or $Pd_2(dba)_3$, and of a suitable ligand. See, for a general reference to the above arylation reaction and operative conditions thereof also inclusive of solvents, catalysts and ligands, J. Am. Chem. Soc., (2003), 125, 6653-55; JOC (2001), 66, 2560-2565; and JOC (2002), 67, 6479-6486.

In addition to the above, it is also clear to the skilled person that, whenever desired, any of the above compounds of formula (I) thus prepared can be further converted into other derivatives of formula (I), as set forth in step (g), by working according to conventional methods.

As an example, the compounds of formula (I)

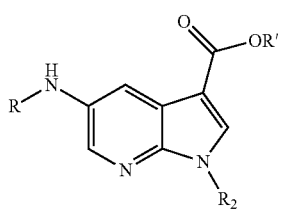
(I)

wherein R and $R_2$ are as set forth above and R' represents a given alkyl group, for instance n-propyl, may be converted into the compounds of formula (I):

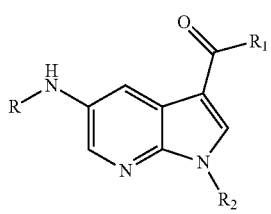
(I)

h) wherein R and $R_2$ are as above defined and $R_1$ is $-OR^c$ with $R^c$ other than n-propyl, through transesterification reactions carried out according to well-known methods, for instance with a suitable compound of formula (XV)

$R^c-OH$  (XV)

under acidic or basic conditions, optionally in the presence of suitable metal based catalysts, like dibutyltin oxide or titanium alkoxides such as, for instance, titanium(IV) ethoxide, titanium(IV) isopropoxide and the like;

i) wherein R and $R_2$ are as above defined and $R_1$ is a group —OH, through acidic or basic hydrolysis.

As an additional example, the compounds of formula (I) wherein R and $R_2$ are as above defined and $R_1$ is a group $-OR^c$ wherein $R^c$ is an alkyl group can be also converted into the corresponding amido derivatives of formula (I)

j) wherein $R_1$ is $-NR^cR^d$, with $R^c$ and $R^d$ as above defined, by treatment with ammonia or with a suitable amine of formula (XVI) or (XVII)

$R^c-NH_2$  (XVI);

$R^cR^dNH$  (XVII)

optionally in the presence of suitable catalysts such as, for instance, sodium cyanide or dimethylamino-pyridine.

Likewise, the compounds of formula (I) wherein R and $R_2$ are as above defined and $R_1$ is a group $-OR^c$ with $R^c$ as hydrogen can be also converted into the corresponding amido derivatives of formula (I), by reaction with any suitable amine $HNR^cR^d$, in the presence of a suitable condensing agent, for instance dicyclohexylcarbodiimide (DCC), 1-ethyl-3-(3'-dimethylaminopropyl)carbodiimide (EDC), O-benzotriazolyltetramethylisouronium tetrafluoroborate (TBTU) or benzotriazol-1-yloxytripyrrolidinophosphonium hexafluorophosphate (PyBOP).

In addition to the above, the compounds of formula (I) wherein $R_2$ is an aryl group (for instance phenyl, pyridyl, optionally substituted phenyl, and the like) or a hydrocarbon chain wherein the first carbon atom directly linked to the pyrrole nitrogen atom is a primary or secondary carbon atom having formula $-CH_2-$ (for instance benzyl, ethyl, n-propyl and the like) or $-CH<$ (for instance diphenylmethyl, isopropyl, and the like), can be also prepared according to an alternative synthetic pathway.

The said pathway comprises, in particular, a different approach for the preparation of the intermediate compound of formula (VII) of step (d).

Therefore, it is a further object of the invention a process for preparing these latter compounds of formula (I) having $R_2$ as an aryl group or a hydrocarbon chain wherein the first carbon atom directly linked to the pyrrole nitrogen atom is a primary or secondary carbon atom, and the pharmaceutically acceptable salts thereof, which process comprises:

k) reacting 1-(phenylsulfonyl)-1H-pyrrolo[2,3-b]pyridine-3-carboxylic acid methyl ester with tetrabutylammonium nitrate (TBAN) in the presence of trifluoroacetic anhydride (TFAA), so as to obtain a compound of formula (XVIII)

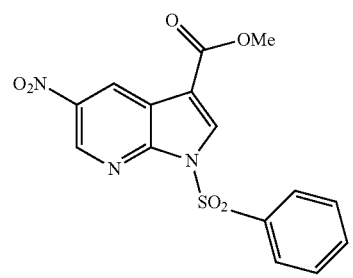
(XVIII)

l) reacting the compound of formula (XVIII) under basic or acidic hydrolysis conditions so as to obtain a compound of formula (XIX) or a salt thereof

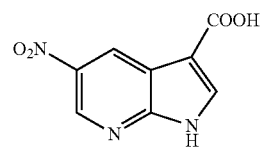
(XIX)

m) reacting the compound of formula (XIX) with a carboxy protecting agent, for instance an esterifying agent, so as to obtain a compound of formula (XX)

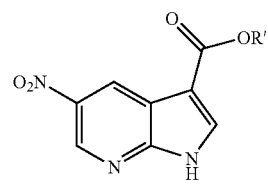
(XX)

wherein R' stands for alkyl, for instance methyl;

n) reacting the compound of formula (XX) with a compound of formula (XXI)

wherein $R_2$ is an aryl group or a hydrocarbon chain having the first carbon atom directly linked to Z' as a primary or secondary carbon atom, and Z' is a halogen atom or any suitable leaving group such as tosyl or mesyl; so as to obtain a compound of formula (VII)

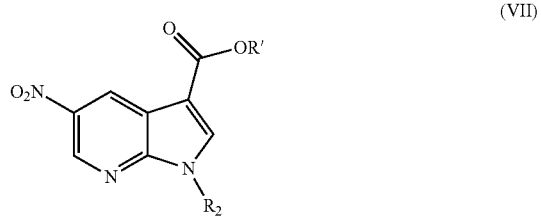

wherein $R_2$ and R' are as above defined;
and then reacting the above compound of formula (VII) according to the remaining steps of the process from (e) to (g).

Also the above process is an analogy process which can be carried out according to well-known methods.

In particular, according to step (k) of the process, the nitration of 1-(phenylsulfonyl)-1H-pyrrolo[2,3-b]pyridine-3-carboxylic acid methyl ester to yield the compound of formula (XVIII) is carried out with tetrabutylammonium nitrate (TBAN) in the presence of trifluoroacetic anhydride (TFAA). The reaction is carried out in a suitable solvent, for instance a halogenated hydrocarbon such as dichloromethane, by working at a temperature ranging from 0° C. to room temperature and for a time varying from about 10 hours to about 30 hours.

According to step (l) of the process, the compound of formula (XVIII) can undergo hydrolysis under basic or acidic conditions. Preferably, the reaction is carried out in the presence of aqueous sodium hydroxide and of 2,2,2-trifluoroethanol (TFE), at a temperature ranging from room temperature to about 90° C. and for a time of from 4 hours to one day. According to the operative conditions being employed, the compound of formula (XVIII) could be obtained either in its acidic form or, alternatively, as a salt.

Preferably, the hydrolysis reaction is carried out under basic conditions, e.g. in the presence of sodium hydroxide, so as to obtain the corresponding sodium salt.

According to step (m) of the process, the compound of formula (XIX) can be esterified according to well-known operative conditions in the presence of suitable alcohols. As an example, this reaction can be performed in the presence of methanol so as to get the corresponding carboxymethyl ester derivative of formula (XX) wherein R' stands for methyl.

Alternatively, the compound of formula (XX) of step (m) wherein R' just stands for methyl can be also prepared through the direct hydrolysis of the compound of formula (XVIII) according to known methods, for instance in the presence of potassium trimethylsylanolate in tetrahydrofuran (THF) or of triethylamine (TEA) in methanol.

Finally, according to step (n) of the process, the compound of formula (XX) is converted into the compound of formula (VII) through reaction with a suitable compound of formula (XXI) wherein $R_2$ and Z' have the above reported meanings. The reaction can be performed in the presence of a suitable base such as, for instance, potassium carbonate, sodium hydride, potassium tertbutoxide, potassium hexamethyldisilazide (KHMDS), lithium hexamethyldisilazide (LHMDS), sodium hexamethyldisilazide (NHMDS), lithium diisopropylamide (LDA) or tert-butylimino(pyrrolidino)phosphorane (BTPP), in a suitable solvent like tetrahydrofuran, dichloromethane, acetonitrile, dimethylformamide, dimethylacetamide, and the like.

According to a preferred embodiment, the reaction is carried out with BTPP in dichloromethane.

Alternative methods are also known in the art to alkylate the pyrrole nitrogen atom of pyrrolo-pyridine cycles, for instance by starting from activated methylidene moieties ($=CH_2$) as reported in Perkin 1, (19), 3317-3324, 2000; or Tetrahedron: Asymmetry, 11(23), 4719-4724, 2000.

From all of the above, it is clear to the skilled person that if a compound of formula (I), prepared according to the above processes comprehensive of any variant thereof, is obtained as an admixture of isomers, their separation into the single isomers of formula (I), carried out according to conventional techniques, is still within the scope of the present invention.

Likewise, the conversion of a compound of formula (I) into a pharmaceutically acceptable salt thereof or, alternatively, the conversion into the free compound (I) of a corresponding salt, according to well-known procedures in the art, is still within the scope of the invention.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

Likewise, the conversion of these latter into the free deprotected compounds may be carried out according to known procedures.

The starting materials of the process object of the present invention, comprehensive of any possible variant, as well as any reactant thereof, are known compounds and if not commercially available per se may be prepared according to well-known methods.

As an example, the formyl-succinonitrile alkaline salt derivative can be prepared as described in the aforementioned cited references [see step (a)], by reacting commercially available butanedinitrile with ethyl formate under basic conditions. Once obtained, the formyl-succinonitrile alkaline salt can be separated from the reaction mixture and then reacted with the amine of formula (II) or, alternatively, directly reacted with the amine of formula (II) in situ, without the need of being isolated, as per step (a) of the process.

In addition, the compound 1-(phenylsulfonyl)-1H-pyrrolo[2,3-b]pyridine-3-carboxylic acid methyl ester can be prepared as described in Tetrahedron Letters 40 (1999), 5853-5854.

Likewise, the compounds of formula (II), (VI), from (VIII) to (XVII), and (XXI) are known or easily obtained according to known methods.

The intermediate compound of formula (XIX) of the process is novel and, hence, represents a further object of the invention.

In addition to the above, the compounds of formula (I) can be advantageously prepared according to combinatorial chemistry techniques widely known in the art, by accomplishing the aforementioned reactions between the intermediates in a serial manner and by working under solid-phase-synthesis (SPS) conditions.

As an example, the intermediate carboxy ester derivatives of formula (VII) being obtained in steps (d) or (n) of the above processes, can be first converted into the free carboxy acid derivatives by means of hydrolysis carried out according to conventional methods, then easily supported onto a polymeric resin, for instance through the formation of a carboxamido group.

The intermediate thus supported may be subsequently reacted according to the remaining steps of the process.

The above synthetic pathway can be summarised as follows:

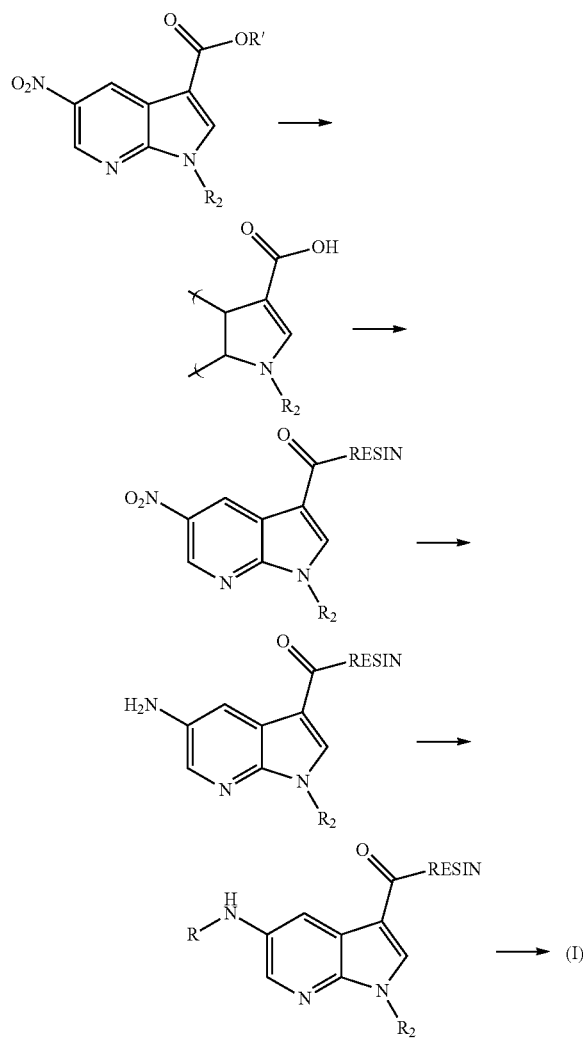

Alternatively, the intermediate compound of formula (XIX) of step (I) can be first supported onto a polymeric resin and then reacted as per the remaining steps of the process, for instance by inserting the $R_2$ moiety in position 1 of the azaindole, by reducing the nitro group in position 5 to amino, by functionalizing the amino group itself and by cleaving the resin so as to obtain the desired compounds of formula (I).

Any of the above reactions is carried out according to known methods, by working as formerly reported, to obtain compounds of formula (I) wherein $R_2$ is an aryl group or a hydrocarbon chain having the first carbon atom attached to the pyrrole nitrogen atom as a primary or secondary carbon atom, as set forth above.

This latter synthetic pathway can be summarised as follows:

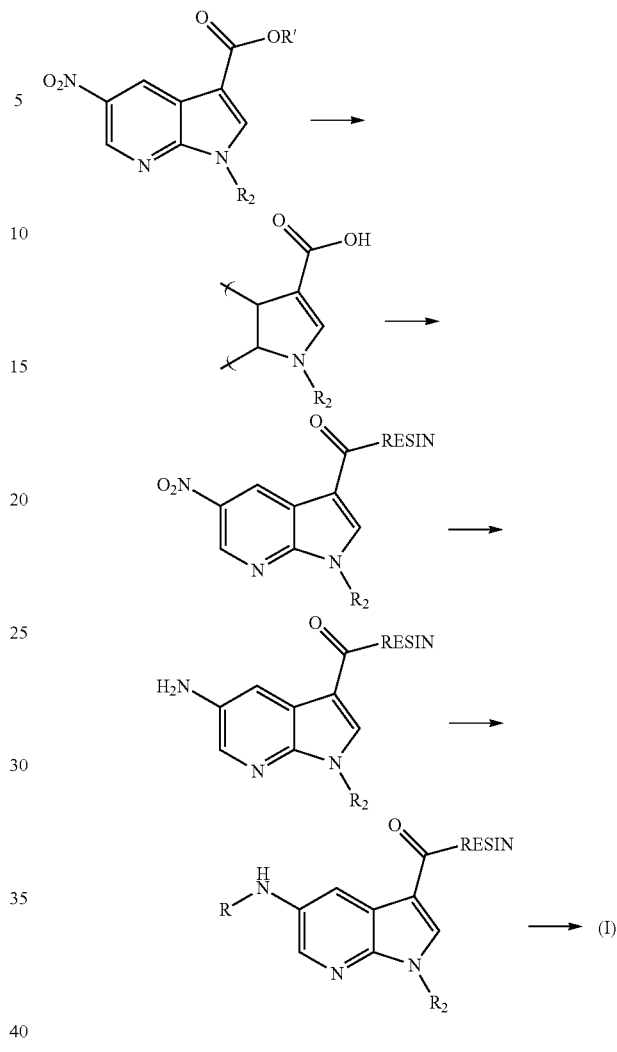

Preferably, the above resin is a commercially available polystyrenic resin including, for instance, Wang resin, Trityl resin, Cl-trityl resin, Rink amide resin, Tentagel OH resin and derivatives thereof.

According to a preferred embodiment of the invention, the polystyrenic resin is a derivatized formyl polystyrenic resin which may be obtained by reacting a commercially available formyl polystyrenic resin, e.g. 4-(4-formyl-3-methoxyphenoxy)butyryl AM resin, with a suitable amino derivative under reductive conditions, for instance in the presence of sodium borohydride and derivatives thereof, substantially as follows:

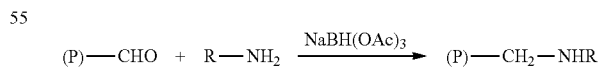

The reaction can be carried out in a suitable solvent such as dichloromethane and in the presence of acetic acid.

The polymer-supported-amino derivatives thus obtained, particularly those, which are referable to as derivatized formyl polystyrenic resin above, are widely known in the art.

In general, amines loaded onto formylpolystyrenic resins also known as Acid Sensitive MethoxyBenzaldehyde polystirene resins (AMEBA resin) are prepared by standard reductive amination in the presence of an excess of amine in TMOF/DCE and NaBH(OAc)$_3$ or AcOH/DMF and NaCNBH$_3$, for instance as reported in Tetrahedron Letters (1997), 38, 7151-7154; J. Am. Chem. Soc. (1998), 120, 5441; and Chem. Eur. J. (1999), 5, 2787.

Therefore, it is a further object of the present invention to provide for a process for preparing the compounds of formula (I), and the pharmaceutically acceptable salts thereof, which process comprises:

o) converting the compound of formula (VII) being prepared according to step (d) or (n) of the aforementioned processes into the corresponding carboxy acid derivative of formula (XXII)

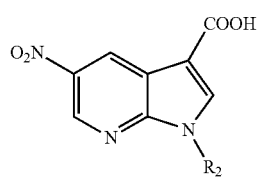

(XXII)

wherein R$_2$ is as set forth in formula (I);

p) reacting the compound of formula (XXII) with a derivatized formyl polystyrenic resin of formula (XXIII)

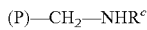

(XXIII)

wherein (P) is the resin and R$^c$ is as set forth in formula (I), so as to obtain a compound of formula (XXIV)

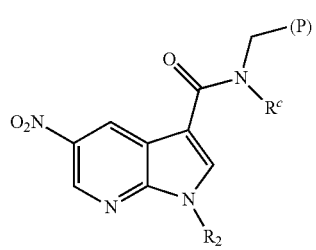

(XXIV)

q) reacting the compound of formula (XXIV) according to step (e) and, optionally, to any one of steps (f.1), (f.2), (f.3) or (f.4), so as to obtain a compound of formula (XXV)

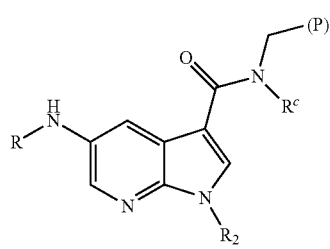

(XXV)

wherein (P), R$_2$ and R$^c$ are as set forth above and R is as defined in formula (I);

r) cleaving the resin from the compound of formula (XXV) under acidic conditions so as to obtain a compound of formula (I) wherein R and R$_2$ are as above defined and R$_1$ is a group —NHR$^c$ wherein R$^c$ is as above defined; and, optionally, s) converting the thus obtained compound of formula (I) into another compound of formula (I) and/or into a pharmaceutically acceptable salts thereof.

According to step (o) of the process, the carboxy ester derivative of formula (VII) is hydrolized to the corresponding carboxy acid by working according to known methods, for instance under acidic or basic conditions.

According to step (p) of the process, the reaction is performed in a suitable solvent, for instance NMP, in the presence of diisopropylethylamine (DIEA) dimethylaminopyridine (DMAP) and of a suitable condensing agent such as, for instance 1-ethyl-3-(3'-dimethylaminopropyl)carbodiimide (EDC), dicyclohexylcarbodiimide (DCC), diisopropylcarbodiimide (DIC) or O-benzotriazolyl tetramethylisouronium tetrafluoroborate (TBTU).

According to step (q), the supported compound of formula (XXIV) is first reduced as per step (e) of the process so as to obtain the amino derivative, and optionally further reacted as formerly indicated, so as to give rise to a variety of compounds functionalised in position 5 of the pyrrolo[2,3-b]pyridine ring. The operative conditions are essentially those formerly reported by working under homogeneous operative conditions.

Resin cleavage according to step (r) may be performed under acidic conditions in the presence of suitable acids such as, for instance, hydrochloric, trifluoroacetic, methanesulfonic or p-toluensulfonic acid.

Another object of the invention is also a process for preparing the compounds of formula (I), and the pharmaceutically acceptable salts thereof, which process comprises:

t) reacting the compound of formula (XIX) being obtained in previous step (I) with a derivatized formyl polystyrenic resin of formula (XXIII)

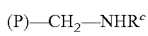

(XXIII)

wherein (P) is the resin and R$^c$ is as set forth in formula (I), so as to obtain a compound of formula (XXVI)

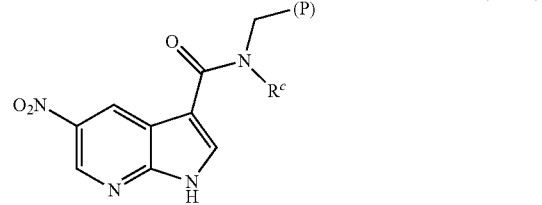

(XXVI)

u) reacting the compound of formula (XXVI) with a compound of formula (XXI) as described in step (n) so as to obtain a compound of formula (XXVII)

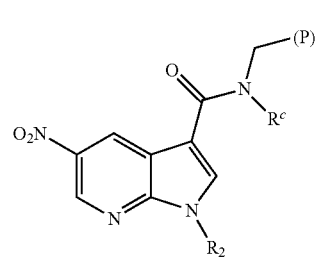

(XXVII)

v) reducing the compound of formula (XXVII) to the corresponding amino derivative of formula (XXVIII) as set forth in step (e)

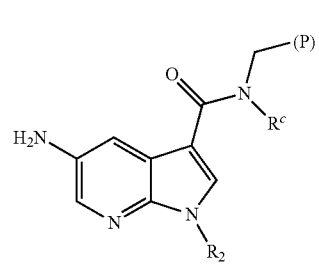

(XXVIII)

and, optionally, converting it according to any one of steps (f.1), (f.2), (f.3) or (f.4), so as to obtain a compound of formula (XXV)

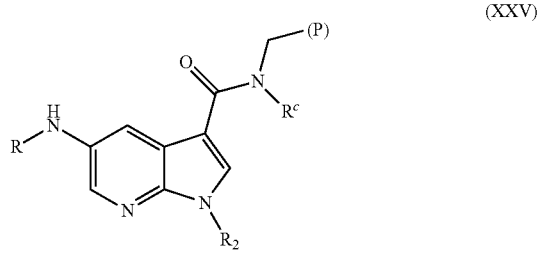

(XXV)

wherein (P), $R_2$ and $R^c$ are as set forth above and R is as defined in formula (I);

w) cleaving the resin from the compound of formula (XXV) according to step (r) and, optionally, converting the thus obtained compound according to step (s).

Clearly, by working according to combinatorial chemistry techniques as formerly indicated, a plurality of compounds of formula (I) can be obtained.

Hence, a further object of the present invention is to provide for a library of two or more compounds of formula (I)

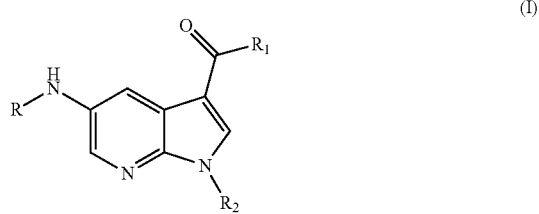

(I)

wherein
R is selected from the group consisting of —$R^a$, —$COR^a$, —$CONR^aR^b$, —$SO_2R^a$ or —$COOR^a$;
$R_1$ is a group —$NR^cR^d$ or —$OR^c$;
wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl or, taken together with the nitrogen atom to which they are bonded, either $R^a$ and $R^b$ as well as $R^c$ and $R^d$ may form an optionally substituted 4 to 7 membered heterocycle, optionally containing one additional heteroatom or heteroatomic group selected from S, O, N or NH;
$R_2$ is a group, optionally further substituted, selected from straight or branched $C_1$-$C_6$ alkyl, $C_2$-$C_6$ alkenyl or $C_2$-$C_6$ alkynyl, $C_3$-$C_6$ cycloalkyl or cycloalkyl $C_1$-$C_6$ alkyl, carbocyclic or heterocyclic aryl or aryl $C_1$-$C_6$ alkyl, heterocycle or heterocycle $C_1$-$C_6$ alkyl; or isomers, tautomers, carriers, metabolites, prodrugs, and pharmaceutically acceptable salts thereof.

According to a preferred embodiment of the invention, the aforementioned library comprises the compounds of formula (I) wherein $R_1$ is a group —$NR^cR^d$ and $R^c$ and $R^d$ are both hydrogen atoms or one of them is a hydrogen atom and the remaining one of $R^c$ or $R^d$ is a straight or branched alkyl or alkenyl group or it is an optionally substituted aryl or arylalkyl group; and R and $R_2$ are as above defined.

Also preferred is a library of compounds of formula (I) wherein R is either a group $R^a$ with $R^a$ as a hydrogen atom or a group —$SO_2R^a$ with $R^a$ as a straight or branched alkyl group or optionally substituted aryl or arylalkyl group; and $R_1$ and $R_2$ are as above defined.

Also preferred is a library of compounds of formula (I) wherein R is a group —$COR^a$ with $R^a$ as a straight or branched alkyl, cycloalkyl or optionally substituted aryl or arylalkyl group; and $R_1$ and $R_2$ are as above defined.

Also preferred is a library of compounds of formula (I) wherein R is a group —$CONR^aR^b$ with one of $R^a$ and $R^b$ as a hydrogen atom and the other of $R^a$ and $R^b$ as a straight or branched alkyl, optionally substituted aryl or arylalkyl group; and $R_1$ and $R_2$ are as above defined.

Also preferred is a library of compounds of formula (I) wherein R is a group —$CONR^aR^b$ and wherein $R^a$ and $R^b$ form, together with the nitrogen atom to which they are bonded, an optionally substituted 6 membered heterocyclic ring; and $R_1$ and $R_2$ are as above defined.

Also preferred is a library of compounds of formula (I) wherein $R_2$ is a straight or branched alkyl or alkenyl group or it is a cycloalkyl, cycloalkyl-alkyl or an optionally substituted aryl or arylalkyl group; and R and $R_1$ are as above defined.

For a general reference to the above libraries of compounds of formula (I) see the experimental section.

From all of the above, it is clear to the skilled person that once a library of pyrrolo[2,3-b]pyridine derivatives is thus prepared, for instance consisting of a few thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

PHARMACOLOGY

The compounds of formula (I) are active as protein kinase inhibitors and are therefore useful, for instance, to restrict the unregulated proliferation of tumour cells. In therapy, they are used in the treatment of various tumours, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting $^{33}$P-labelled biotinylated product is allowed to bind to streptavidin-coated SPA beads (biotin capacity 130 pmol/mg), and light emitted was measured in a scintillation counter.

Inhibition Assay of CDK2/Cyclin a Activity

Kinase reaction: 4 µM in house biotinylated histone H1 (Sigma # H-5505) substrate, 10 µM ATP (0.1 microCi $P^{33}\gamma$-ATP), 1.1 nM Cyclin A/CDK2 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 µl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: inhibitors were tested at different concentrations ranging from 0.0015 to 10 μM. Experimental data were analyzed by the computer program GraphPad Prizm using the four parameter logistic equation:

$$y = \text{bottom} + (\text{top} - \text{bottom})/(1 + 10^{((\log IC50 - x) * \text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM MgCl$_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{V_m \cdot A \cdot B}{\alpha \cdot K_a \cdot K_b + \alpha \cdot K_a \cdot B + a \cdot K_b \cdot A + A \cdot B + \alpha \cdot \frac{K_a}{K_i} \cdot I \cdot \left(K_b + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds are characterized on a panel of ser/thre kinases strictly related to cell cycle (cdk2/cyclin E, cdk1/cyclin B1, cdk5/p25, cdk4/cyclin D1), and also for specificity on MAPK, PKA, EGFR, IGF1-R, Aurora-2 and Cdc7.

Inhibition Assay of cdk2/Cyclin E Activity

Kinase reaction: 10 μM in house biotinylated histone H1 (Sigma # H-5505) substrate, 30 μM ATP (0.3 microCi P$^{33}$γ-ATP), 4 ng GST-Cyclin E/CDK2 complex, inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After incubation for 60 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of CDK1/Cyclin B1 Activity

Kinase reaction: 4 μM in house biotinylated histone H1 (Sigma # H-5505) substrate, 20 μM ATP (0.2 microCi P$^{33}$γ-ATP), 3 ng Cyclin B/CDK1 complex, inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After 20 min at r.t. incubation, reaction was stopped by 100 μl PBS+32 mM EDTA+0.1% Triton X-100+ 500 μM ATP, containing 1 mg SPA beads. Then a volume of 110 μl is transferred to Optiplate.

After 20 min. incubation for substrate capture, 100 μl 5M CsCl were added to allow stratification of beads to the top of the Optiplate and let stand 4 hours before radioactivity counting in the Top-Count instrument.

IC50 determination: see above

Inhibition Assay of CDK5/P25 Activity

The inhibition assay of cdk5/p25 activity is performed according to the following protocol.

Kinase reaction: 10 μM biotinylated histone H1 (Sigma # H-5505) substrate, 30 μM ATP (0.3 microCi P$^{33}$γ-ATP), 15 ng CDK5/p25 complex, inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of CDK4/Cyclin D1 Activity

Kinase reaction: 0.4 uM μM mouse GST-Rb (769-921) (# sc-4112 from Santa Cruz) substrate, 10 μM ATP (0.5 μCi P$^{33}$γ-ATP), 100 ng of baculovirus expressed GST-cdk4/GST-Cyclin D1, suitable concentrations of inhibitor in a final volume of 50 μl buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 μl EDTA 120 mM.

Capture: 60 μl were transferred from each well to MultiScreen plate, to allow substrate binding to phosphocellulose filter. Plates were then washed 3 times with 150 μl/well PBS Ca$^{++}$/Mg$^{++}$ free and filtered by MultiScreen filtration system.

Detection: filters were allowed to dry at 37° C., then 100 μl/well scintillant were added and $^{33}$P labeled Rb fragment was detected by radioactivity counting in the Top-Count instrument.

IC50 determination: see above

Inhibition Assay of MAPK Activity

Kinase reaction: 10 μM in house biotinylated MBP (Sigma # M-1891) substrate, 15 μM ATP (0.15 microCi P$^{33}$γ-ATP), 30 ng GST-MAPK (Upstate Biotechnology #14-173), inhibitor in a final volume of 30 μl buffer (TRIS HCl 10 mM pH 7.5, MgCl$_2$ 10 mM, DTT 7.5 mM+0.2 mg/ml BSA) were added to each well of a 96 U bottom. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of PKA Activity

Kinase reaction: 10 μM in house biotinylated histone H1 (Sigma # H-5505) substrate, 10 μM ATP (0.2 microM $P^{33}\gamma$-ATP), 0.45 U PKA (Sigma #2645), inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom. After incubation for 90 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above

Inhibition Assay of EGFR Activity

Kinase reaction: 10 μM in house biotinylated MBP (Sigma # M-1891) substrate, 2 μM ATP (0.04 microCi $P^{33}\gamma$-ATP), 36 ng insect cell expressed GST-EGFR, inhibitor in a final volume of 30 μl buffer (Hepes 50 mM pH 7.5, $MgCl_2$ 3 mM, $MnCl_2$ 3 mM, DTT 1 mM, $NaVO_3$ 3 μM, +0.2 mg/ml BSA) were added to each well of a 96 U bottom. After incubation for 20 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

$IC_{50}$ determination: see above

Inhibition Assay of IGF1-R Activity

The inhibition assay of IGF1-R activity is performed according to the following protocol.

Enzyme activation: IGF1-R must be activated by autophosphorylation before starting the experiment. Just prior to the assay, a concentrated enzyme solution (694 nM) is incubated for half a hour at 28° C. in the presence of 100 μM ATP and then brought to the working dilution in the indicated buffer.

Kinase reaction: 10 μM biotinylated IRS1 peptide (PRIMM) substrate, 0-20 μM inhibitor, 6 μM ATP, 1 microCi $^{33}$P-ATP, and 6 nM GST-IGF1-R (pre-incubated for 30 min at room temperature with cold 60 μM cold ATP) in a final volume of 30 μl buffer (50 mM HEPES pH 7.9, 3 mM $MnCl_2$, 1 mM DTT, 3 μM $NaVO_3$) were added to each well of a 96 U bottom well plate. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

Inhibition Assay of Aurora-2 Activity

Kinase reaction: 8 μM biotinylated peptide (4 repeats of LRRWSLG), 10 μM ATP (0.5 uCi $P^{33}\gamma$-ATP), 7.5 ng Aurora 2, inhibitor in a final volume of 30 μl buffer (HEPES 50 mM pH 7.0, $MgCl_2$ 10 mM, 1 mM DTT, 0.2 mg/ml BSA, 3 μM orthovanadate) were added to each well of a 96 U bottom well plate. After 60 minutes at room temperature incubation, reaction was stopped and biotinylated peptide captured by adding 100 μl of bead suspension.

Stratification: 100 μl of CsCl2 5 M were added to each well and let stand 4 hour before radioactivity was counted in the Top-Count instrument.

IC50 determination: see above

Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:

10 μl substrate (biotinylated MCM2, 6 μM final concentration)

10 μl enzyme (Cdc7/Dbf4, 17.9 nM final concentration)

10 μl test compound (12 increasing concentrations in the nM to μM range to generate a dose-response curve)

10 μl of a mixture of cold ATP (2 μM final concentration) and radioactive ATP (1/5000 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 60 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above.

The compounds of formula (I) of the present invention, suitable for administration to a mammal, e.g. to humans, are administered by the usual routes and the dosage level depends upon the age, weight, conditions of the patient and the administration route.

For example, a suitable dosage adopted for oral administration of a compound of formula (I) preferably ranges from about 10 to about 500 mg per dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors and the like, optionally within liposomal formulations thereof.

If formulated as a fixed dose, such combination products employ the compounds of this invention within the dosage range described above and the other pharmaceutically active agent within the approved dosage range.

Compounds of formula (I) can also be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms can contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration can also be e.g. syrups, emulsions and suspensions.

The syrups can contain as carrier, for example, saccharose or saccharose with glycerin and/or mannitol and/or sorbitol.

The suspensions and the emulsions can contain as carrier, for example, a natural gum, agar, sodium alginate, pectin, methylcellulose, carboxymethylcellulose, or polyvinyl alcohol.

The suspension or solutions for intramuscular injections can contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories can contain together with the active compound a pharmaceutically acceptable carrier, e.g. cocoa butter, polyethylene glycol, a polyoxyethylene sorbitan fatty ester surfactant or lecithin.

The following examples are herewith intended to better illustrate the present invention without posing any limitation to it.

Experimental Section

General Methods

Flash Chromatography was performed on silica gel (Merck grade 9395, 60A). The high pressure liquid chromatography retention times (HPLC: r.t. values) were determined by:
Method 1 (HPLC_1):
Instrumentation: Hewlett Packard 1312A binary pump; Gilson 215 autosampler fitted with a 1 ml syringe, Polymer Labs PL1000 Evaporative Light Scattering Detector (ELSD), and a Micromass ZMD mass spectrometer operating in Electrospray positive ionisation mode. The LC eluent is split and approximately 200 µl/min enters the mass spectrometer, 800 µl/min to the ELS.

Chromatographic condition: HPLC mobile phases consisting of 0.1% trifluoroacetic acid in HPLC grade water (A) and 0.1% trifluoroacetic acid in HPLC grade acetonitrile (B). The HPLC gradient is shown in the table below

| Time (mins) | % A | % B |
|---|---|---|
| 0.0 | 100 | 0 |
| 1.8 | 5 | 95 |
| 2.1 | 5 | 95 |
| 2.3 | 100 | 0 |
| 2.4 | 100 | 0 |

| | |
|---|---|
| Run time: | 2.4 minutes |
| Flow rate: | 1 ml/min |
| Injection vol: | 3 µl |
| Column temperature: | ambient (20° C.) |
| Column: | 50 × 2.0 mm Hypersil C18 BDS; 5 µm |
| ELS Detector: | Nebuliser Temperature 80° C. Evaporation temperature 90° C. Gas Flow 1.5 l/hr |
| MS Detector: | m/z 150-800 @ 0.5 secs/scan, 0.1 second interscan delay Cone voltage 25 V, Source Temp. 140° C. Drying Gas 350 l/hr |

ELSD retention times (HPLC r.t.) are given in minutes. Mass are given as m/z ratio.
Method 2 (HPLC_2):
Instrumentation: Waters 2790 HPLC system equipped with a 996 Waters PDA detector and Micromass mod. ZQ single quadrupole mass spectrometer, equipped with an electrospray (ESI) ion source.

Chromatographic condition: RP18 Waters X Terra (4.6×50 mm, 3.5 µm) column; Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 µl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, the compounds have been purified by preparative HPLC on a Waters Symmetry C18 (19×50 mm, 5 µm) column using a waters preparative HPLC 600 equipped with a 996 Waters PDA detector and a Micromass mod. ZQ single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 ml/min.

$^1$H-NMR spectrometry was performed on a Bruker AVANCE 400 MHz single bay instrument with gradients. It is equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

As formerly indicated, several compounds of formula (I) of the invention have been synthesized in parallel, according to combinatorial chemistry techniques.

In this respect, some compounds thus prepared have been conveniently and unambiguously identified, as per the coding system of tables from IV to IX, together with HPLC retention time (methods 1 and 2) and mass.

Each code, which identifies a single specific compound of formula (I), consists of four units A-M-B-C.

A represents any substituent $R_1$—[see formula (I)] and is attached to the rest of the azaindole moiety through the carbon atom of the carbonyl group so as to get azaindole derivatives being substituted in position 3; each A radical (substituent) is represented in the following table I.

B represents any substituent R—[see formula (I)] and is attached to the rest of the azaindole moiety through the nitrogen atom of the NH group so as to get azaindole derivatives being substituted in position 5; each B radical (substituent) is represented in the following table II.

C represents any substituent $R_2$—[see formula (I)] and is attached to the rest of the azaindole moiety through the indolic nitrogen atom so as to get azaindole derivatives being substituted in position 1; each C radical (substituent) is represented in the following table III.

M refers to the central core of the trivalent azaindole moiety being substituted in position 1 by groups C, in position 3 (through the carbonyl group) by groups A, and in position 5 (through the NH group) by groups B, substantially as follows:

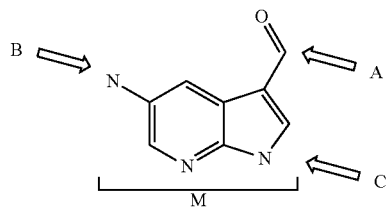

For ease of reference, each A, B or C groups of tables I, II and III has been identified with the proper chemical formula also indicating the point of attachment with the rest of the molecule M.

Just as an example, the compound A3-M-B5-C2 of table IV (entry 1) represents an azaindole M being substituted in position 5 by the group B5 (through the NH group), in position 3 by the group A3 (through the CO group) and in position 1 by the group C2; likewise, the compound A9-M-B9-C2 of table IX (entry 40) represents an azaindole M being substituted in position 5 by the group B9 (through the NH group), in position 3 by the group A9 (through the CO group) and in position 1 by the group C2, as follows:

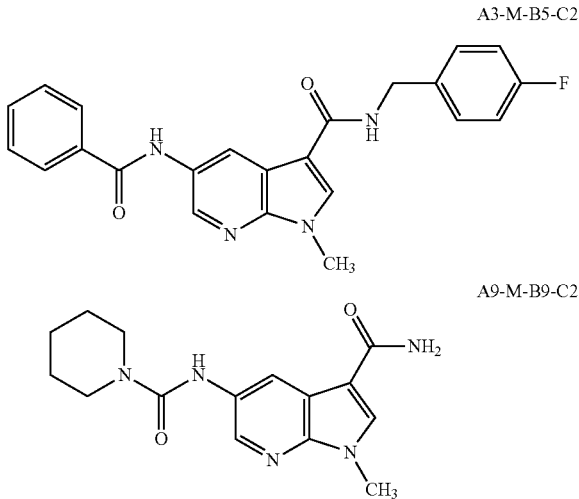

TABLE I

A groups

| Fragment | Code |
|---|---|
| M-NH-CH2-C6H5 | A1 |
| CH2=CH-CH2-NH-M | A2 |
| 4-F-C6H4-CH2-NH-M | A3 |
| (CH3)2CH-NH-M | A4 |
| 4-CH3-C6H4-CH2-NH-M | A5 |
| CH3CH2CH2-NH-M | A6 |
| 3-CH3O-C6H4-CH2-NH-M | A7 |
| CH3CH2-O-CH2CH2-NH-M | A8 |
| H2N-M | A9 |

TABLE II

B groups

| Fragment | Code |
|---|---|
| CH3-S(O)2-M | B1 |
| 4-CH3-C6H4-S(O)2-M | B2 |
| CH3CH2-S(O)2-M | B3 |

TABLE II-continued

| B groups | |
|---|---|
| Fragment | Code |
| 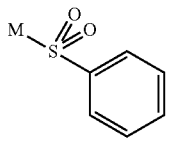 | B4 |
| 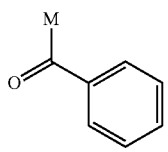 | B5 |
|  | B6 |
| 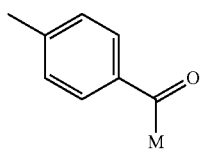 | B7 |
| 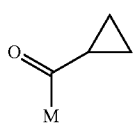 | B8 |
| 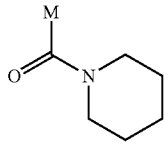 | B9 |
| 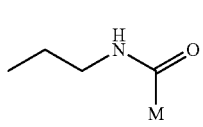 | B10 |
| 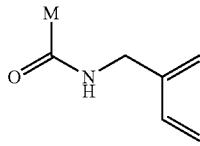 | B11 |
| 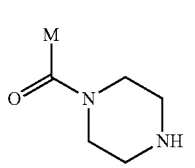 | B12 |
| H | B13 |
| 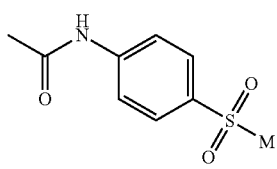 | B14 |

TABLE II-continued

| B groups | |
|---|---|
| Fragment | Code |
| 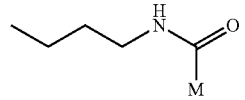 | B15 |

TABLE III

| C groups | |
|---|---|
| Fragment | Code |
| 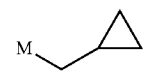 | C1 |
|  | C2 |
|  | C3 |
| 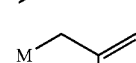 | C4 |
| 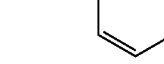 | C5 |
| 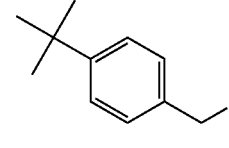 | C6 |
|  | C7 |
| 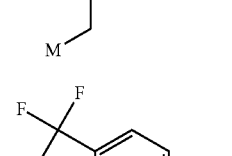 | C8 |
| 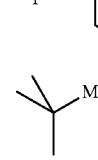 | C9 |

EXAMPLE 1

Preparation of 1-tert-butyl-5-nitro-1H-pyrrolo[2,3-b]pyridine-3-carbonitrile

To a solution of 5.85 g (35.8 mmol) of 5-amino-1-tert-butyl-1H-pyrrole-3-carbonitrile, being prepared as disclosed in Org. Proc. Res. Dev., 7(2), 209-213, 2003, in 120 mL of n-propanol, it was added sodium nitromalonaldehyde (6.02 g, 43.0 mmol) portionwise under stirring at room temperature. The resulting mixture was treated dropwise with 37% hydrochloric acid (4.6 mL, 55.2 mmol) and heated at 100° C. for 2 hours. The reaction mass was concentrated under vacuum to ⅓ of the initial volume and kept at 4° C. for 18 hours. The precipitate was filtered off, washed thoroughly with 15% aqueous ethanol (35 mL), water (5 mL) and finally dried to afford 7.14 g of the title compound as a light brown solid.
m.p.=216-218° C.
Yield=81.5%
$^1$H-NMR (DMSO): 1.77 (s, 9H), 8.81 (s, 1H), 8.90 (d, 1H, J=2.63 Hz), 9.26 (d, 1H, J=2.63 Hz).

EXAMPLE 2

Preparation of 1-tert-butyl-5-nitro-1H-pyrrolo[2,3-b]pyridine-3-carboxylic acid propyl ester To a suspension of 5.0 g (20.47 mmol) of 1-tert-butyl-5-nitro-1H-pyrrolo[2,3-b]pyridine-3-carbonitrile in 125 mL of n-propanol, 7.78 g of p-toluensulfonic acid were added under stirring. The mixture was heated at reflux for 40 hours and then it was cooled to room temperature and diluted with 70 mL of tert-butyl methyl ether. The precipitate was filtered off and the clear filtrate was concentrated under vacuum to a small volume (about 40-50 mL). The suspension was cooled to −5/0° C. and kept at this temperature for 2 hours. The solid was filtered, washed with 20 mL of 1:1 mixture of n-propanol and tert-butyl methyl ether and dried to afford 5.50 g of the title compound as a cream-colored solid.
m.p. 116-120° C.
Yield=88%
$^1$H-NMR (DMSO): 1.00 (t, 3H), 1.70-1.80 (m, 2H), 1.80 (s, 9H), 4.27 (t, 2H), 8.42 (s, 1H), 9.01 (d, 1H, J=2.63 Hz), 9.22 (d, 1H, J=2.63 Hz).

EXAMPLE 3

Preparation of 1-tert-butyl-5-nitro-1H-pyrrolo[2,3-b]pyridine-3-carboxylic acid

To a suspension of 5.00 g (16.38 mmol) of 1-tert-butyl-5-nitro-1H-pyrrolo[2,3-b]pyridine-3-carboxylic acid propyl ester in 50 mL of 95° ethanol, it was added 2M NaOH (50 mL; 100 mmol) under stirring. The mixture was heated to reflux for 1 hour obtaining the complete consumption of the substrate. The resulting solution was cooled to room temperature and concentrated under reduced pressure to a slurry that was diluted with 250 mL of water and washed with 100 mL of a 1:1 mixture of diethyl ether and ethyl acetate. The aqueous layer was treated with 5M HCl (37 mL; 185 mmol) under efficient stirring at room temperature. The precipitate was filtered off, washed twice with 10 mL of water and dried so as to afford 3.84 g of the title compound as a white solid.
m.p.=278-281° C. dec.
Yield=89%
$^1$H-NMR (DMSO): 1.79 (s, 9H), 8.36 (s, 1H), 9.03 (d, 1H, J=2.63 Hz), 9.20 (d, 1H, J=2.63 Hz), 12.77 (bs, 1H).

EXAMPLE 4

Preparation of methyl 5-nitro-1-(phenylsulfonyl)-1H-pyrrolo[2,3-b]pyridine-3-carboxylate To an ice-cooled solution of 187.7 g (0.616 mol) of tetrabutylammonium nitrate in 2.07 L of dichloromethane, trifluoroacetic anhydride (85.7 mL, 0.616 mol) was added dropwise over a period of 25 minutes, under nitrogen. This mixture was slowly transferred, via cannula, to a preformed solution of 150.0 g (0.474 mol) of 1-(phenylsulfonyl)-1H-pyrrolo[2,3-b]pyridine-3-carboxylic acid methyl ester in 2.7 L of dichloromethane at +4° C. The reaction mixture was stirred at +4° C. for 4 hours and then kept at this temperature for additional 23 hours. The cold reaction mass was poured in 2.3 L of water and stirred for 1 hour. The aqueous layer was separated and extracted again with 1 L of dichloromethane. The combined organic extracts were concentrated under vacuum to a thick yellow suspension, which was treated with 1.05 L of methanol. The slurry was cooled at 0° C. and stirred for further 1 hour before it was filtered, washed with methanol and dried to afford 128 g of pure title compound as a woolly yellow solid (Yield=74.7%). m.p.=195-196° C. $^1$H-NMR (DMSO): 3.91 (s, 3H), 7.64-7.69 (m, 2H), 7.76-7.81 (m, 1H), 8.25-8.27 (m, 2H), 8.74 (s, 1H), 8.96 (d, 1H, J=2.58 Hz), 9.27 (d, 1H, J=2.58 Hz).

EXAMPLE 5

Preparation of disodium 5-nitro-1H-pyrrolo[2,3-b]pyridine-3-carboxylate

To a suspension of 95.7 g (0.265 mol) of the compound of example 4 in 1.34 L of 2,2,2-trifluoroethanol, 0.545 L of 17% NaOH were added over a period of 40 minutes under vigorous stirring. The yellow-orange mixture was heated at reflux for 16 hours and then it was cooled to 0° C. and stirred for 2 additional hours. The precipitate was filtered off, washed with acetone and dried to afford 79.8 g of the title compound as an orange crystalline solid
(Yield=93.1% as tetrahydrate). m.p. >230° C.
$^1$H-NMR (DMSO): 7.83 (bs, 1H), 8.89 (d, 1H, J=2.80 Hz), 9.07 (bs, 1H).

EXAMPLE 6

Preparation of 5-nitro-1H-pyrrolo[2,3-b]pyridine-3-carboxylic acid

To a clear solution of the compound of example 5 (88.10 g, 0.35 mol) in 2.65 L of water, it was added dropwise concentrated HCl (52.6 mL, 0.526 mol) diluted with 105 mL of water over a period of 50 minutes under efficient stirring at ambient temperature. The resulting suspension was cooled at +4° C. and stirred for further 1 hour. The precipitate was filtered off, washed with water and finally dried to give 55.6 g of the title compound as a light-yellow powder (Yield=98.5% (title 95%)).
m.p.=282-285° C. dec.
$^1$H-NMR (DMSO): 8.41 (d, 1H, J=2.83 Hz), 9.00 (d, 1H, J=2.59 Hz), 9.16 (d, 1H, J=2.59 Hz), 12.5-13.0 (bs, 1H), 13.14 (s, 1H).

EXAMPLE 7

General Procedure: Loading of 4-Fluorobenzylamine (Corresponding to Fragment A3 of Table I) onto Acid Sensitive Methoxy Benzaldehyde Polystyrene Resin (AMEBA II Resin)

4-(4-Formyl-3-methoxyphenoxy)butyryl AM resin [copoly(styrene-1% dvb) 100-200 mesh] (1.5 g, 1 eq, loading 0.94 mmol/g) was swollen in DCM and then filtered. A mixture of THF/DCM (4:1, 15 ml), 4-fluorobenzylamine (6 eq.) and AcOH (6 eq.) was added. After 15 minutes, NaBH(OAc)$_3$ was added and the reaction was shaken over night at room

EXAMPLE 8

Step 8.1: Loading of the Azaindole Scaffold onto the Resin of Example 7

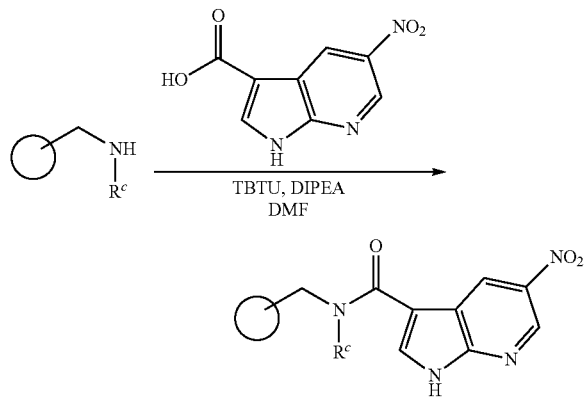

To the resin (1.5 g, 0.77 mmol/g, 1.16 mmol) of example 7 in anhydrous DMF (15 ml), it was added 5-nitro-1H-pyrrolo[2,3-b]pyridine-3-carboxylic acid (0.359 g, 1.73 mmol), TBTU (0.556 g, 1.73 mmol) and DIPEA (0.44 g, 3.48 mmol). The reaction mixture was shaken at room temperature for 20 hours and then the resin was isolated by filtration. The resin was washed sequentially with DMF (25 ml), DCM (25 ml), DMF (25 ml), DCM (25 ml), MeOH (25 ml), DCM (25 ml), MeOH (25 ml), TBME (25 ml×2) and dried in vacuo to give the resin bound 7-azaindole (1.70 g).

Resin Loading Check

Resin loading check was carried out to demonstrate the complete loading of the building block onto the resin and that no oligomerization has occurred whilst coupling with TBTU. Benzoyl chloride was used in order to cap unreacted resin loaded amine (i.e. 4-fluorobenzylamine, for example 8) and to acylate the 1-NH azaindole. The absence of benzamide (i.e. N-(4-fluorobenzyl)benzamide, for example 8) in the cleaved mixture demonstrates the quantitative loading of the scaffold onto the resin. The presence of 1-N-benzoylazaindole or of 1-NH-azaindole, demonstrate that no homocoupling of the 3-carboxy-5-nitro-7-azaindole has occurred during the resin loading step. To the resin obtained following the procedure described in example 8 (step 8.1) (0.035 g, 0.027 mmol) in DCM (1 ml) it was added DIPEA (0.035 g, 0.265 mmol) and benzoyl chloride (0.038 g, 0.265 mmol). The reaction mixture was shaken for 4 hours and the resin isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (1 ml of 60% TFA/DCM for 20 minutes) to give an off white solid (0.007 g, 64%).

LCMS (HPLC_1) (N-benzoylated indole): m/z 419 [M+H]+ @ r.t. 1.56 min (97% by ELS detection).

Step 8.2: N-Alkylation of the Resin Bound 7-Azaindole

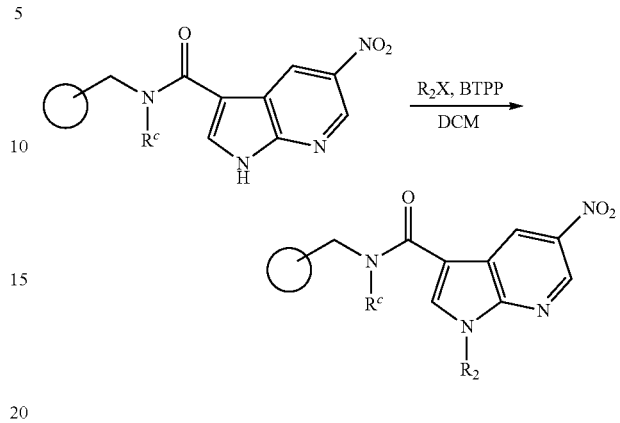

To the resin (0.85 g, corresponding to 0.58 mmol) of step (8.1) in anhydrous DCM (20 ml) it was added BTPP (0.540 g, 1.74 mmol) and iodomethane ($R_2$ corresponding to fragment C2 of table III, 0.821 g, 5.8 mmol). The reaction mixture was shaken at room temperature for 20 hours and then the resin was isolated by filtration. The resin was washed sequentially with DMF (25 ml), DCM (25 ml), DMF (25 ml), DCM (25 ml), MeOH (25 ml), DCM (25 ml), MeOH (25 ml), DCM (25 ml), MeOH (25 ml), TBME (25 ml×2) and dried in vacuo to give the resin bound N-methylated-7-azaindole (0.85 g). 0.01 g of the resin were cleaved (1 ml of 60% TFA/DCM for 20 minutes) to give an off-white solid (0.0015 g, 60%).

LCMS: m/z 329 [M+H]+ @ r.t. 1.72 min (94% @ 215 nm).

Step 8.3: Reduction of the Nitro Group

To the resin of step (8.2) (0.85 g) in NMP (10 ml), it was added tin(II) chloride dihydrate (1.3 g, 5.8 mmol). The reaction mixture was shaken at room temperature for 20 hours and then the resin was isolated by filtration. The resin was washed sequentially with DMF (10 ml), DCM (10 ml), DMF (10 ml), DCM (10 ml), MeOH (10 ml), water (10 ml), MeOH (10 ml), DCM (10 ml), MeOH (10 ml), DCM (10 ml), MeOH (10 ml), TBME (10 ml×2) and dried in vacuo to give the corresponding resin bound N-methylated-5-amino-7-azaindole (0.825 g). 0.01 g of the resin were cleaved (1 ml of 60% TFA/DCM for 20 minutes) to give an off-white solid (0.0015 g, 65%).

LCMS (HPLC_1): m/z 299 [M+H]+ @ r.t. 0.97 min (100% by ELS detection).

The above resin bound azaindole was further reacted according to the alternative steps below so as to get carboxamido, sulfonamido and ureido derivatives.

Preparation of A3-M-B5-C2

Step 8.4: Capping with Acid Chloride Derivatives

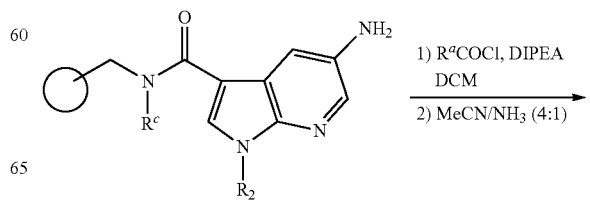

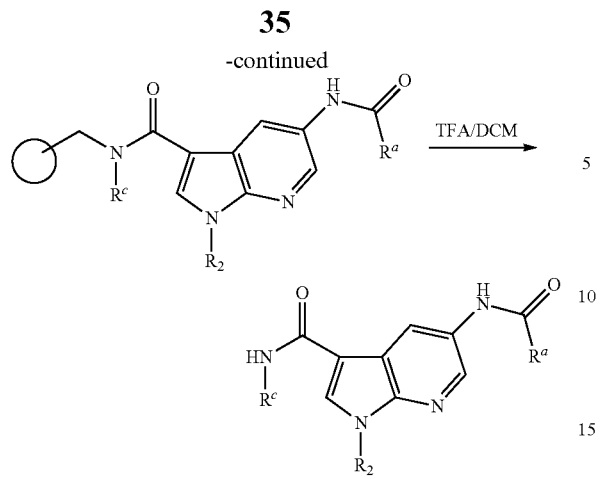

To the resin of step (8.3) (0.11 g, corresponding to 0.077 mmol) in DCM (1 ml) it was added Hunig's base (0.050 g, 0.385 mmol) followed by benzoyl chloride (group —COR$^a$ corresponding to fragment B5 of table II, 0.054 g, 0.385 mmol). The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The resin was shaken in acetonitrile/ammonia solution (1 ml, 4:1) for 4 hours and then isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin [60% TFA/DCM, 3×(3×0.5 ml)] to give an off white solid (0.026 g, 84%) corresponding to compound A3-M-B5-C2 (see entry 1 of table IV below). LCMS (HPLC_1): m/z 403 [M+H]$^+$ @ r.t. 1.29 min (100% by ELS detection).

Following the procedure described in example 8 and by using any proper reactant as per the process of the invention that is, by supporting any suitable amine onto the resin, by functionalizing position 1 of the azaindole moiety with any suitable reactant, by acylating the amino function in position 5 of the azaindole moiety with any suitable acyl chloride derivative and by finally carrying out resin cleavage, the following compounds of table IV were also prepared.

TABLE IV

| Entry | Compound | HPLC method | r.t. (min) | [M + H]$^+$ |
|---|---|---|---|---|
| 1 | A3-M-B5-C2 | HPLC_1 | 1.29 | 403 |
| 2 | A3-M-B6-C2 | HPLC_1 | 1.04 | 341 |
| 3 | A4-M-B5-C2 | HPLC_1 | 1.1 | 337 |
| 4 | A4-M-B6-C2 | HPLC_1 | 0.85 | 275 |
| 5 | A7-M-B5-C2 | HPLC_1 | 1.26 | 415 |
| 6 | A7-M-B6-C2 | HPLC_1 | 1.02 | 353 |
| 7 | A6-M-B5-C2 | HPLC_1 | 1.11 | 337 |
| 8 | A6-M-B6-C2 | HPLC_1 | 0.85 | 275 |
| 9 | A1-M-B5-C2 | HPLC_1 | 1.26 | 385 |
| 10 | A1-M-B6-C2 | HPLC_1 | 1.01 | 323 |
| 11 | A5-M-B5-C2 | HPLC_1 | 1.32 | 399 |
| 12 | A5-M-B6-C2 | HPLC_1 | 1.1 | 337 |
| 13 | A8-M-B5-C2 | HPLC_1 | 1.07 | 367 |
| 14 | A8-M-B6-C2 | HPLC_1 | 0.83 | 305 |
| 15 | A2-M-B5-C2 | HPLC_1 | 1.09 | 335 |
| 16 | A2-M-B6-C2 | HPLC_1 | 0.82 | 273 |
| 17 | A3-M-B5-C5 | HPLC_1 | 1.5 | 479 |
| 18 | A3-M-B6-C5 | HPLC_1 | 1.3 | 417 |
| 19 | A4-M-B5-C5 | HPLC_1 | 1.38 | 413 |
| 20 | A4-M-B6-C5 | HPLC_1 | 1.15 | 351 |
| 21 | A7-M-B5-C5 | HPLC_1 | 1.48 | 491 |
| 22 | A7-M-B6-C5 | HPLC_1 | 1.28 | 429 |
| 23 | A6-M-B5-C5 | HPLC_1 | 1.38 | 413 |
| 24 | A6-M-B6-C5 | HPLC_1 | 1.15 | 351 |
| 25 | A1-M-B5-C5 | HPLC_1 | 1.49 | 461 |
| 26 | A1-M-B6-C5 | HPLC_1 | 1.28 | 399 |
| 27 | A5-M-B5-C5 | HPLC_1 | 1.54 | 475 |
| 28 | A5-M-B6-C5 | HPLC_1 | 1.34 | 413 |
| 29 | A8-M-B5-C5 | HPLC_1 | 1.34 | 443 |
| 30 | A8-M-B6-C5 | HPLC_1 | 1.11 | 381 |
| 31 | A2-M-B5-C5 | HPLC_1 | 1.36 | 411 |
| 32 | A2-M-B6-C5 | HPLC_1 | 1.13 | 349 |

Preparation of A3-M-B1-C2

Step 8.5: Capping with Sulfonyl Chloride Derivatives

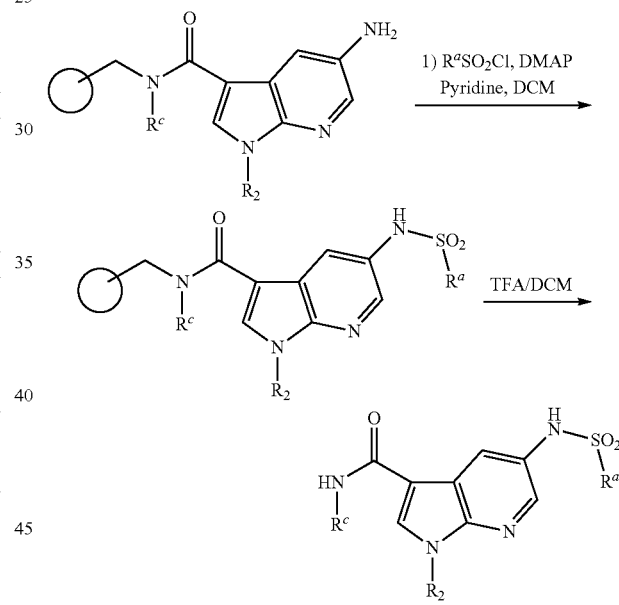

To the resin of step (8.3) (0.11 g, corresponding to 0.077 mmol) in DCM (1 ml) it was added pyridine (0.030 g, 0.385 mmol), DMAP (0.001 g, 0.0077 mmol) and methane sulfonyl chloride (group —SO$_2$R$^a$ corresponding to fragment B1 of table II, 0.044 g, 0.385 mmol). The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin [60% TFA/DCM, 3×(3×0.5 ml)] to give an off white solid (0.024 g, 83%) corresponding to compound A3-M-B1-C2 (see entry 33 of table V below).

LCMS (HPLC_1): m/z 377 [M+H]$^+$ @ r.t. 1.12 min (97.5% by ELS detection).

Following the procedure described in example 8 and by using any proper reactant as per the process of the invention that is, by supporting any suitable amine onto the resin, by functionalizing position 1 of the azaindole moiety with any suitable reactant, by sulfonylating the amino function in position 5 of the azaindole moiety with any suitable sulfonyl chloride derivative and by finally carrying out resin cleavage, the following compounds of table V were also prepared.

TABLE V

| Entry | Compound | HPLC method | r.t. (min) | $[M + H]^+$ |
|---|---|---|---|---|
| 33 | A3-M-B1-C2 | HPLC_1 | 1.12 | 377 |
| 34 | A3-M-B4-C2 | HPLC_1 | 1.3 | 439 |
| 35 | A4-M-B1-C2 | HPLC_1 | 0.9 | 311 |
| 36 | A4-M-B4-C2 | HPLC_1 | 1.14 | 373 |
| 37 | A7-M-B1-C2 | HPLC_1 | 1.09 | 389 |
| 38 | A7-M-B4-C2 | HPLC_1 | 1.28 | 451 |
| 39 | A6-M-B1-C2 | HPLC_1 | 0.91 | 311 |
| 40 | A6-M-B4-C2 | HPLC_1 | 1.14 | 373 |
| 41 | A1-M-B1-C2 | HPLC_1 | 1.08 | 359 |
| 42 | A1-M-B4-C2 | HPLC_1 | 1.28 | 421 |
| 43 | A5-M-B1-C2 | HPLC_1 | 1.17 | 373 |
| 44 | A5-M-B4-C2 | HPLC_1 | 1.34 | 435 |
| 45 | A8-M-B1-C2 | HPLC_1 | 0.89 | 341 |
| 46 | A8-M-B4-C2 | HPLC_1 | 1.1 | 403 |
| 47 | A2-M-B1-C2 | HPLC_1 | 0.89 | 309 |
| 48 | A3-M-B1-C5 | HPLC_1 | 1.37 | 453 |
| 49 | A3-M-B4-C5 | HPLC_1 | 1.51 | 515 |
| 50 | A4-M-B1-C5 | HPLC_1 | 1.24 | 387 |
| 51 | A4-M-B4-C5 | HPLC_1 | 1.41 | 449 |
| 52 | A7-M-B1-C5 | HPLC_1 | 1.35 | 465 |
| 53 | A7-M-B4-C5 | HPLC_1 | 1.49 | 527 |
| 54 | A6-M-B1-C5 | HPLC_1 | 1.23 | 387 |
| 55 | A6-M-B4-C5 | HPLC_1 | 1.4 | 449 |
| 56 | A1-M-B1-C5 | HPLC_1 | 1.35 | 435 |
| 57 | A1-M-B4-C5 | HPLC_1 | 1.49 | 497 |
| 58 | A5-M-B1-C5 | HPLC_1 | 1.41 | 449 |
| 59 | A5-M-B4-C5 | HPLC_1 | 1.54 | 511 |
| 60 | A8-M-B1-C5 | HPLC_1 | 1.19 | 417 |
| 61 | A8-M-B4-C5 | HPLC_1 | 1.37 | 479 |
| 62 | A2-M-B1-C5 | HPLC_1 | 1.21 | 385 |
| 63 | A2-M-B4-C5 | HPLC_1 | 1.38 | 447 |

Step 8.6: Phenylcarbamate (and Bis-Phenylcarbamate) Formation

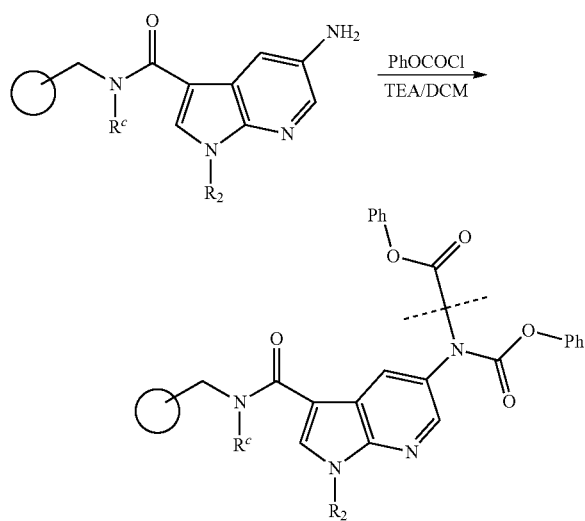

To the resin of step (8.3) (0.25 g, corresponding to 0.19 mmol) in DCM (10 ml) it was added triethylamine (0.39 g, 3.85 mmol) and phenyl chloroformate (0.603 g, 3.85 mmol). The reaction mixture was shaken at room temperature for 20 hours and then the resin was isolated by filtration. The resin was washed sequentially with DMF (10 ml), DCM (10 ml), DMF (10 ml), DCM (10 ml), MeOH (10 ml), DCM (10 ml), MeOH (10 ml), DCM (10 ml), MeOH (10 ml), TBME (10 ml×2) and dried in vacuo to give the corresponding resin bound azaindole (0.275 g) which was further reacted according to the following step.

Preparation of A3-M-B9-C2

Step 8.7: Formation of Ureido Derivatives

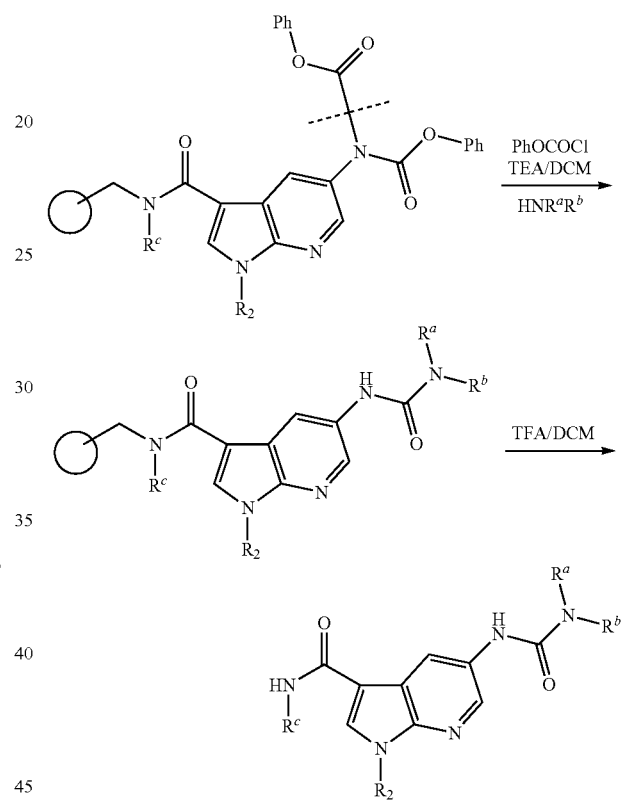

To the resin of step (8.6) (0.11 g, corresponding to 0.077 mmol) in DCM (1 ml) it was added piperidine (group —CONR$^a$R$^b$ corresponding to fragment B9 of table II, 0.131 g, 1.54 mmol). The reaction mixture was shaken at room temperature for 72 hours and then the resin was isolated by filtration. The resin was washed sequentially with DMF (1 ml), DCM (1 DMF (1 DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (60% TFA/DCM, 3×(3×0.5 ml)) to give an off white solid (0.027 g, 87%) corresponding to compound A3-M-B9-C2 (see entry 64 of table VI below).

LCMS (HPLC_1): m/z 410 [M+H]$^+$ @ r.t. 1.21 min (86% by ELS detection).

Following the procedure described in example 8 and by using any proper reactant as per the process of the invention, that is by supporting any suitable amine onto the resin, by functionalizing position 1 of the azaindole moiety with any suitable reactant, by preparing the carbamate derivative in position 5 of the azaindole moiety, by converting it into the corresponding ureido derivative through reaction with any suitable amine and by finally carrying out resin cleavage, the following compounds of table VI were also prepared.

TABLE VI

| Entry | Compound | HPLC method | r.t. (min) | [M + H]+ |
|---|---|---|---|---|
| 64 | A3-M-B9-C2 | HPLC_1 | 1.21 | 410 |
| 65 | A3-M-B10-C2 | HPLC_1 | 1.15 | 384 |
| 66 | A4-M-B10-C2 | HPLC_1 | 0.95 | 318 |
| 67 | A1-M-B10-C2 | HPLC_1 | 1.12 | 366 |
| 68 | A5-M-B10-C2 | HPLC_1 | 1.19 | 380 |
| 69 | A3-M-B9-C5 | HPLC_1 | 1.44 | 486 |
| 70 | A7-M-B9-C5 | HPLC_1 | 1.42 | 498 |
| 71 | A1-M-B9-C5 | HPLC_1 | 1.42 | 468 |
| 72 | A1-M-B10-C5 | HPLC_1 | 1.36 | 442 |

EXAMPLE 9

Step 9.1: Loading of the Azaindole Scaffold onto Rink Resin

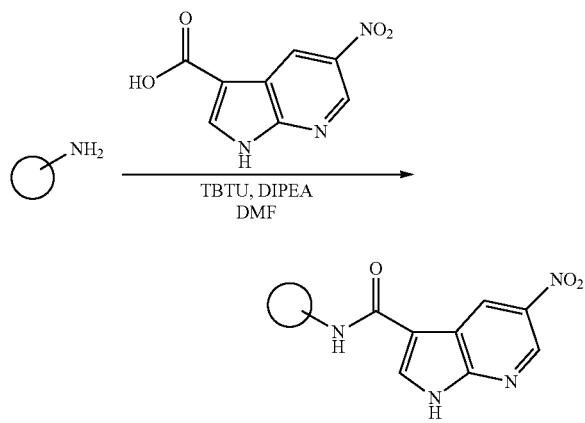

To the Rink resin (corresponding to fragment A9 of table I, 11 g, 0.85 mmol/g, 9.35 mmol) in anhydrous DMF (15 ml), 5-nitro-1H-pyrrolo[2,3-b]pyridine-3-carboxylic acid (2.9 g, 14.03 mmol), TBTU (4.5 g, 14.03 mmol) and DIPEA (3.62 g, 28.05 mmol) were added. The reaction mixture was shaken at room temperature for 20 hours and then the resin was isolated by filtration. The resin was washed sequentially with DMF (25 ml), DCM (25 ml), DMF (25 ml), DCM (25 ml), MeOH (25 ml), DCM (25 ml), MeOH (25 ml), DCM (25 ml), MeOH (25 ml), TBME (25 ml×2) and dried in vacuo to give the resin bound 7-azaindole (12.5 g). 0.01 g of the resin were cleaved (1 ml of 40% TFA/DCM) to give an off-white solid (0.0014 mg, 82%).

LCMS (HPLC_1): m/z 207 [M+H]+ @ r.t. 0.79 min (89% by ELS detection).

Step 9.2: N-Alkylation of the Resin Bound 7-Azaindole

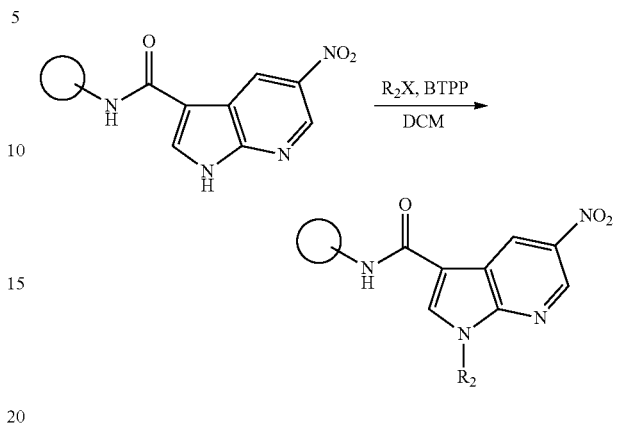

To the resin of step (9.1) (1.6 g, corresponding to 1.36 mmol) in anhydrous DCM (20 ml), BTPP (1.278 g, 4.08 mmol) and iodomethane (group $R_2$ corresponding to fragment C2 of table III, 1.938 g, 13.6 mmol) were added. The reaction mixture was shaken at room temperature for 20 hours and then the resin was isolated by filtration. The resin was washed sequentially with DMF (20 ml), DCM (20 ml), DMF (20 ml), DCM (20 ml), MeOH (20 ml), DCM (20 ml), MeOH (20 ml), DCM (20 ml), MeOH (20 ml), TBME (20 ml×2) and dried in vacuo to give the resin bound N-alkylated-7-azaindole (1.8 g). 0.01 g of the resin were cleaved (1 ml of 40% TFA/DCM) to give an off-white solid (0.0015 g, 83%).

LCMS: m/z 221 [M+H]+ and 262 [M+MeCN+H]+ @ r.t. 1.35 min (65% @ 215 nm).

Step 9.3: Reduction of the Nitro Group

To the resin of step (9.2) (1.6 g) in NMP (20 ml) it was added tin(II) chloride dihydrate (3.1 g, 13.6 mmol). The reaction mixture was shaken at room temperature for 20 hours and then the resin was isolated by filtration. The resin was washed sequentially with DMF (20 ml), DCM (20 ml), DMF (20 ml), DCM (20 ml), MeOH (20 ml), water (20 ml), MeOH (20 ml), DCM (20 ml), MeOH (20 ml), DCM (20 ml), MeOH (20 ml), TBME (20 ml×2) and dried in vacuo to give the resin bound 5-amino-7-azaindole (0.825 g). 0.01 g of the resin were cleaved (1 ml of 40% TFA/DCM) to give an off-white solid (0.0012 g, 75%).

LCMS (HPLC_1): m/z 191 [M+H]+ @ r.t. 0.59 min (100% by ELS detection).

The above resin bound azaindole was further reacted according to the alternative steps below so as to get carboxamido, sulfonamido and ureido derivatives.

Preparation of A9-M-B5-C2

Step 9.4: Capping with Acid Chloride Derivatives

To the resin of step (9.3) (0.11 g, corresponding to 0.085 mmol) in DCM (1 ml) it was added Hunig's base (0.055 g, 0.425 mmol) followed by benzoyl chloride (group —COR$^a$ corresponding to fragment B5 of table II, 0.060 g, 0.425 mmol). The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The resin was shaken in acetonitrile/ammonia solution (1 ml, 4:1) for 4 hours and then isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (40% TFA/DCM, 3×0.5 ml) to give an off white solid (0.017 g, 68%) corresponding to compound A9-M-B5-C2 (see entry 3 of table VII below).

LCMS (HPLC_1): m/z 295 [M+H]$^+$ @ r.t. 0.92 min (88% by ELS detection).

By working in an analogous way and by using any suitable starting material and reactant of the process, the following compounds of table VII were also prepared.

TABLE VII

| Entry | Compound | HPLC method | r.t. (min) | [M + H]$^+$ |
|---|---|---|---|---|
| 1 | A9-M-B5-C1 | HPLC_1 | 1.09 | 335 |
| 2 | A9-M-B7-C1 | HPLC_1 | 1.17 | 349 |
| 3 | A9-M-B5-C2 | HPLC_1 | 0.92 | 295 |
| 4 | A9-M-B7-C2 | HPLC_1 | 1.02 | 309 |
| 5 | A9-M-B5-C3 | HPLC_1 | 0.99 | 309 |
| 6 | A9-M-B7-C3 | HPLC_1 | 1.07 | 323 |
| 7 | A9-M-B8-C3 | HPLC_1 | 0.84 | 273 |
| 8 | A9-M-B5-C4 | HPLC_1 | 1.03 | 321 |
| 9 | A9-M-B5-C5 | HPLC_1 | 1.2 | 371 |
| 10 | A9-M-B5-C6 | HPLC_1 | 1.45 | 427 |
| 11 | A9-M-B7-C6 | HPLC_1 | 1.51 | 441 |
| 12 | A9-M-B8-C6 | HPLC_1 | 1.35 | 391 |
| 13 | A9-M-B5-C7 | HPLC_1 | 1.27 | 385 |
| 14 | A9-M-B6-C7 | HPLC_1 | 1.05 | 323 |
| 15 | A9-M-B8-C7 | HPLC_1 | 1.15 | 349 |
| 16 | A9-M-B5-C8 | HPLC_1 | 1.34 | 439 |
| 17 | A9-M-B7-C8 | HPLC_1 | 1.41 | 453 |
| 18 | A9-M-B8-C8 | HPLC_1 | 1.24 | 403 |
| 19 | A9-M-B13-C2 | HPLC_1 | 0.21 | 191 |
| 20 | A9-M-B13-C5 | HPLC_1 | 0.86 | 267 |
| 21 | A9-M-B13-C6 | HPLC_1 | 1.14 | 323 |
| 22 | A9-M-B13-C8 | HPLC_1 | 1.04 | 335 |

Preparation of A9-M-B4-C2

Step 9.5: Capping with Sulfonyl Chloride Derivatives

To the resin of step (9.3) (0.11 g, corresponding to 0.085 mmol) in DCM (1 ml), pyridine (0.034 g, 0.425 mmol), DMAP (0.001 g, 0.0085 mmol) and benzene sulfonyl chloride (group —SO2Ra corresponding to fragment B4 of table III, 0.075 g, 0.385 mmol) were added. The reaction mixture was shaken at room temperature for 20 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (40% TFA/DCM, 3×0.5 ml) to give an off white solid (0.022 g, 80%) corresponding to compound A9-M-B4-C2 (see entry 24 of table VIII below).

LCMS (HPLC_1): m/z 331 [M+H]$^+$ @ r.t. 0.96 min (81% by ELS detection).

By working in an analogous way and by using any suitable starting material and reactant of the process, the following compounds of table VIII were also prepared.

TABLE VIII

| Entry | Compound | HPLC method | r.t. (min) | [M + H]$^+$ |
|---|---|---|---|---|
| 23 | A9-M-B1-C1 | HPLC_1 | 0.92 | 309 |
| 24 | A9-M-B4-C2 | HPLC_1 | 0.96 | 331 |
| 25 | A9-M-B3-C3 | HPLC_1 | 0.83 | 297 |
| 26 | A9-M-B1-C4 | HPLC_1 | 0.85 | 295 |
| 27 | A9-M-B3-C4 | HPLC_1 | 0.89 | 309 |
| 28 | A9-M-B1-C5 | HPLC_1 | 1.04 | 345 |
| 29 | A9-M-B3-C5 | HPLC_1 | 1.08 | 359 |
| 30 | A9-M-B4-C5 | HPLC_1 | 1.23 | 407 |
| 31 | A9-M-B2-C6 | HPLC_1 | 1.52 | 477 |
| 32 | A9-M-B3-C6 | HPLC_1 | 1.36 | 415 |
| 33 | A9-M-B4-C6 | HPLC_1 | 1.47 | 463 |
| 34 | A9-M-B3-C7 | HPLC_1 | 1.16 | 373 |
| 35 | A9-M-B1-C8 | HPLC_1 | 1.21 | 413 |
| 36 | A9-M-B2-C8 | HPLC_1 | 1.41 | 489 |
| 37 | A9-M-B3-C8 | HPLC_1 | 1.24 | 427 |
| 38 | A9-M-B4-C8 | HPLC_1 | 1.36 | 475 |

Step 9.6: Phenyl Carbamate (and Bis Phenyl Carbamate) Formation

To the resin of step (9.3) (0.60 g, corresponding to 0.51 mmol) in DCM (10 ml), triethylamine (1.03 g, 10.2 mmol) and phenyl chloroformate (1.597 g, 10.2 mmol) were added. The reaction mixture was shaken at room temperature for 20 hours and then the resin was isolated by filtration. The resin was washed sequentially with DMF (10 ml), DCM (10 ml), DMF (10 ml), DCM (10 ml), MeOH (10 ml), DCM (10 ml), MeOH (10 ml), DCM (10 ml), MeOH (10 ml), TBME (10 ml×2) and dried in vacuo to give the resin bound 7-azaindole (0.65 g). 0.01 g of the resin were cleaved (1 ml of 40% TFA/DCM) to give an off-white solid (0.001 g, 69%).

LCMS (HPLC_1) (mono and bis phenyl carbamates observed): m/z 311 [M+H]$^+$ @ r.t. 1.03 min (77% by ELS detection) and m/z 431 [M+H]$^+$ @ r.t. 1.31 min (12% by ELS detection).

Preparation of A9-M-B9-C2

Step 9.7: Formation of Ureido Derivatives

To the resin of step (9.6) (0.11 g, 0.085 mmol) in DCM (1 ml) it was added piperidine (group —CONR$^a$R$^b$ corresponding to fragment B9 of table II, 0.143 g, 1.7 mmol). The reaction mixture was shaken at room temperature for 72 hours and then the resin was isolated by filtration. The resin was washed sequentially with DMF (1 ml), DCM (1 ml), DMF (1 ml), DCM (1 ml), MeOH (1 ml), water (1 ml), MeOH (1 ml), DCM (1 ml), MeOH (1 ml), DCM (1 ml), MeOH (1 ml), TBME (1 ml×2) and then air dried. The product was cleaved from the resin (40% TFA/DCM, 3×0.5 ml) to give an off white solid (0.020 g, 79%) corresponding to compound A9-M-B9-C2 (see entry 40 of table IX below).

LCMS (HPLC_1): m/z 302 [M+H]$^+$ @ r.t. 0.86 min (91% by ELS detection).

By working in an analogous way and by using any suitable starting material and reactant of the process, the following compounds of table IX were also prepared.

TABLE IX

| Entry | Compound | HPLC method | r.t. (min) | [M + H]+ |
|---|---|---|---|---|
| 39 | A9-M-B9-C1 | HPLC_1 | 1.02 | 342 |
| 40 | A9-M-B9-C2 | HPLC_1 | 0.86 | 302 |
| 41 | A9-M-B10-C2 | HPLC_1 | 0.79 | 276 |
| 42 | A9-M-B11-C2 | HPLC_1 | 0.95 | 324 |
| 43 | A9-M-B9-C3 | HPLC_1 | 0.92 | 316 |
| 44 | A9-M-B10-C3 | HPLC_1 | 0.84 | 290 |
| 45 | A9-M-B11-C3 | HPLC_1 | 0.99 | 338 |
| 46 | A9-M-B9-C4 | HPLC_1 | 0.96 | 328 |
| 47 | A9-M-B10-C4 | HPLC_1 | 0.89 | 302 |
| 48 | A9-M-B11-C4 | HPLC_1 | 1.04 | 350 |
| 49 | A9-M-B9-C5 | HPLC_1 | 1.13 | 378 |
| 50 | A9-M-B12-C5 | HPLC_1 | 0.88 | 379 |
| 51 | A9-M-B10-C5 | HPLC_1 | 1.07 | 352 |
| 52 | A9-M-B11-C5 | HPLC_1 | 1.19 | 400 |
| 53 | A9-M-B9-C6 | HPLC_1 | 1.39 | 434 |
| 54 | A9-M-B12-C6 | HPLC_1 | 1.14 | 435 |
| 55 | A9-M-B10-C6 | HPLC_1 | 1.34 | 408 |
| 56 | A9-M-B11-C6 | HPLC_1 | 1.42 | 456 |
| 57 | A9-M-B9-C7 | HPLC_1 | 1.2 | 392 |
| 58 | A9-M-B12-C7 | HPLC_1 | 0.95 | 393 |
| 59 | A9-M-B10-C7 | HPLC_1 | 1.14 | 366 |
| 60 | A9-M-B11-C7 | HPLC_1 | 1.25 | 414 |
| 61 | A9-M-B9-C8 | HPLC_1 | 1.29 | 446 |
| 62 | A9-M-B12-C8 | HPLC_1 | 1.04 | 447 |
| 63 | A9-M-B10-C8 | HPLC_1 | 1.23 | 420 |
| 64 | A9-M-B11-C8 | HPLC_1 | 1.33 | 468 |

EXAMPLE 10

Step 10.1: Loading of the Azaindole Scaffold onto the Resin

To the AMEBA II resin (0.1 g, 1 mmol/g, 0.1 mmol) in DCM/DMF (1:1, 2 ml), 1-tert-butyl-5-nitro-1H-pyrrolo[2,3-b]pyridine-3-carboxylic acid (3 eq), DIC (1.5 eq) DMAP (0.5 eq) and DIPEA (1 eq) were added. The reaction mixture was shaken at room temperature for 20 hours and then the resin was isolated by filtration. The resin was washed sequentially with DMF (2 ml), DCM (2 ml), DMF (2 ml), DCM (2 ml), MeOH (2 ml), DCM (2 ml), MeOH (2 ml), DCM (2 ml), MeOH (2 ml), DCM (2 ml) and dried in vacuo to give the resin bound 7-azaindole.

Step 10.2: Reduction of the Nitro Group

To the resin of step (10.1) (0.1 g, 1 mmol/g, 0.1 mmol) in NMP (2 ml), it was added tin(II) chloride dihydrate (10 eq). The reaction mixture was shaken at room temperature for 20 hours and then the resin was isolated by filtration. The resin was washed sequentially with DMF (5 ml), DCM (5 ml), DMF (5 ml), DCM (5 ml), MeOH (5 ml), water (5 ml), MeOH (5 ml), DCM (5 ml), MeOH (5 ml), DCM (5 ml), MeOH (5 ml), DCM (5 ml) and dried in vacuo to give the resin bound 5-amino-7-azaindole. 0.01 g of the resin were cleaved (1 ml of 20% TFA/DCM for 20 minutes) to give the corresponding amine.

LCMS (HPLC_2): m/z 323 [M+H]+, r.t. 5.2 min.

Preparation of A1-M-B6-C9

Step 10.3: Capping with Acyl Chloride Derivatives

To the resin of step (10.2) (0.1 g, corresponding to 0.1 mmol) in DCM (1 ml) it was added Hunig's base (5 eq) followed by acetyl chloride (group —COR$^a$ corresponding to fragment B6 of table II, 5 eq). The reaction mixture was shaken at room temperature for 20 hours and then the resin was isolated by filtration. The resin was washed sequentially with DMF (2 ml), DCM (2 ml), DMF (2 ml), DCM (2 ml), MeOH (2 ml), water (2 ml), MeOH (2 ml), DCM (2 ml), MeOH (2 ml), DCM (2 ml), MeOH (2 ml), DCM (2 ml), MeOH (2 ml), DCM (1 ml×2) and then dried. The resin was shaken in acetonitrile/ammonia solution (1 ml, 4:1) for 4 hours and then isolated by filtration. The compound 5-(acetylamino)-N-benzyl-1-tert-butyl-1H-pyrrolo[2,3-b]pyridine-3-carboxamide, having code A1-M-B6-C9, was cleaved from the resin [20% TFA/DCM, 3×(3×0.5 ml)].

LCMS (HPLC_2): m/z 365 [M+H]+, r.t. 5.4 min.

Preparation of A1-M-B14-C9

Step 10.4: Capping with Sulfonyl Chloride Derivatives

To the resin of step (10.2) (0.1 g, corresponding to 0.1 mmol) in DCM (1 ml), DIPEA (5 eq), DMAP (0.1 eq) and 4-(acetylamino)benzenesulfonyl chloride (group —SO$_2$R$^a$ corresponding to fragment B14 of table II, 5 eq) were added. The reaction mixture was shaken at room temperature for 20 hours and then the resin was isolated by filtration. The resin was washed sequentially with DMF (2 ml), DCM (2 ml), DMF (2 ml), DCM (2 ml), MeOH (2 ml), water (2 ml), MeOH (2 ml), DCM (2 ml), MeOH (2 ml), DCM (2 ml), MeOH (2 ml), DCM (1 ml×2) and then dried under vacuum. The compound 5-({[4-(acetylamino)phenyl]sulfonyl}amino)-N-benzyl-1-tert-butyl-1H-pyrrolo[2,3-b]pyridine-3-carboxamide, having code A1-M-B14-C9, was cleaved from the resin (20% TFA/DCM, 3×(3×0.5 ml).

LCMS (HPLC_2): m/z 520 [M+H]+, r.t. 6.0 min.

Preparation of A1-M-B15-C9

Step 10.5: Capping with Isocyanate Derivatives

To the resin of step (10.3) (0.1 g, corresponding to 0.1 mmol) in DCM (1 ml), it was added butylisocyanate (group —CONR$^a$R$^b$ corresponding to fragment B15 of table II, 10 eq). The reaction mixture was shaken at room temperature for 48 hours and then the resin was isolated by filtration. The resin was washed sequentially with DMF (2 ml), DCM (2 ml), DMF (2 ml), DCM (2 ml), MeOH (2 ml), water (2 ml), MeOH (2 ml), DCM (2 ml), MeOH (2 ml), DCM (2 ml), MeOH (2 ml), DCM (1 ml×2) and then dried under vacuum. The compound N-benzyl-1-tert-butyl-5-{[(butylamino)carbonyl]amino}-1H-pyrrolo[2,3-b]pyridine-3-carboxamide, having code A1-M-B15-C9, was cleaved from the resin 20% TFA/DCM, 3×(3×0.5 ml).

LCMS (HPLC_2): m/z 422 [M+H]+, r.t. 6.5 min.

The invention claimed is:
1. A method for inhibiting one or more protein kinases selected from the group consisting of ACK1, AKT, JAK2, MET, MST4, NEK6, RET and IGF-1R which comprises contacting said kinase with an effective amount of a pyrrolo[2,3-b]pyridine represented by formula (I)

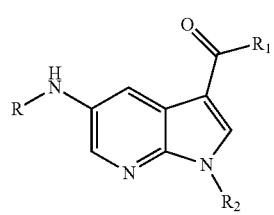

(I)

wherein
R is —R$^a$, —COR$^a$, —CONR$^a$R$^b$, —SO$_2$R$^a$ or —COOR$^a$;
R$_1$ is —NR$^c$R$^d$ or —OR$^c$;

wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, $R^a$ and $R^b$ as well as $R^C$ and $R^d$, may form a 1,3-dioxolane, pyran, pyrrolidine, pyrroline, imidazoline, imidazolidine, pyrazolidine, pyrazoline, piperidine, piperazine, morpholine, tetrahydrofuran, hexamethylenediamine, 1,4-hexahydrodiazepine or azetidine group;

$R_2$ is a group, optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl;

or isomers, tautomers, and pharmaceutically acceptable salts thereof.

2. A method for inhibiting protein kinase activity which comprises contacting the said kinase with an effective amount of a compound of formula (I) having the formula

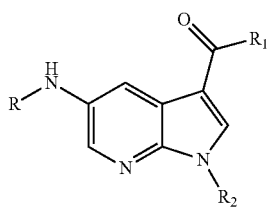

(I)

wherein
R is —$R^a$, —$COR^a$, —$CONR^aR^b$, —$SO_2R^a$ or —$COOR^a$;
$R_1$ is —$NR^cR^d$ or —$OR^c$;
wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, $R^a$ and $R^b$ as well as $R^C$ and $R^d$, may form a 1,3-dioxolane, pyran, pyrrolidine, pyrroline, imidazoline, imidazolidine, pyrazolidine, pyrazoline, piperidine, piperazine, morpholine, tetrahydrofuran, hexamethylenediamine, 1,4-hexahydrodiazepine or azetidine group;

$R_2$ is a group, optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl;

or isomers, tautomers, and pharmaceutically acceptable salts thereof.

3. A library comprised of two or more compounds of formula (I)

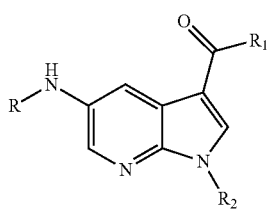

(I)

wherein
R is selected from the group consisting of —$R^a$, —$COR^a$, —$CONR^aR^b$, —$SO_2R^a$ or —$COOR^a$;
$R_1$ is a group —$NR^cR^d$ or —$OR^c$;
wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl, aryl $C_1$-$C_6$ alkyl, or heterocycle or heterocycle $C_1$-$C_6$— alkyl or, taken together with the nitrogen atom to which they are bonded, $R^a$ and $R^b$ as well as $R^C$ and $R^d$, may form a 1,3-dioxolane, pyran, pyrrolidine, pyrroline, imidazoline, imidazolidine, pyrazolidine, pyrazoline, piperidine, piperazine, morpholine, tetrahydrofuran, hexamethylenediamine, 1,4-hexahydrodiazepine or azetidine group;

$R_2$ is a group, optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl;

or isomers, tautomers, and pharmaceutically acceptable salts thereof.

4. The library according to claim 3 wherein $R_1$ is a group —$NR^cR^d$ and $R^c$ and $R^d$ are both hydrogen atoms or one of them is a hydrogen atom and the remaining one of $R^c$ or $R^d$ is alkyl or alkenyl group, or an optionally substituted aryl or arylalkyl group.

5. The library according to claim 3 wherein R is hydrogen or a group —$SO_2R^a$ wherein $R^a$ is a straight or branched alkyl or optionally substituted aryl or arylalkyl group.

6. The library according to claim 3 wherein R is a group —$COR^a$ wherein $R^a$ is a straight or branched alkyl, cycloalkyl or optionally substituted aryl or arylalkyl group.

7. The library according to claim 3 wherein R is —$CONR^aR^b$ wherein one of $R^a$ and $R^b$ is hydrogen and the other of $R^a$ and $R^b$ is a straight or branched alkyl or optionally substituted aryl or arylalkyl group.

8. The library according to claim 3 wherein R is —$CONR^aR^b$, $R^a$ and $R^b$ form, together with the nitrogen atom to which they are bonded, an optionally substituted 6 membered heterocyclic ring.

9. The library according to claim 3 wherein $R_2$ is alkyl, alkenyl group, cycloalkyl, cycloalkyl-alkyl or an optionally substituted aryl or arylalkyl group.

10. The library according to claim 3 wherein the compound in the library is a compound listed in Table IV, V, VI, VII, VIII or IX:

A3-M-B5-C2
A3-M-B6-C2
A4-M-B5-C2
A4-M-B6-C2
A7-M-B5-C2
A7-M-B6-C2
A6-M-B5-C2
A6-M-B6-C2
A1-M-B5-C2
A1-M-B6-C2
A5-M-B5-C2
A5-M-B6-C2
A8-M-B5-C2
A8-M-B6-C2
A2-M-B5-C2
A2-M-B6-C2
A3-M-B5-C5
A3-M-B6-C5
A4-M-B5-C5
A4-M-B6-C5

-continued

A7-M-B5-C5
A7-M-B6-C5
A6-M-B5-C5
A6-M-B6-C5
A1-M-B5-C5
A1-M-B6-C5
A5-M-B5-C5
A5-M-B6-C5
A8-M-B5-C5
A8-M-B6-C5
A2-M-B5-C5
A2-M-B6-C5
A3-M-B1-C2
A3-M-B4-C2
A4-M-B1-C2
A4-M-B4-C2
A7-M-B1-C2
A7-M-B4-C2
A6-M-B1-C2
A6-M-B4-C2
A1-M-B1-C2
A1-M-B4-C2
A5-M-B1-C2
A5-M-B4-C2
A8-M-B1-C2
A8-M-B4-C2
A2-M-B1-C2
A3-M-B1-C5
A3-M-B4-C5
A4-M-B1-C5
A4-M-B4-C5
A7-M-B1-C5
A7-M-B4-C5
A6-M-B1-C5
A6-M-B4-C5
A1-M-B1-C5
A1-M-B4-C5
A5-M-B1-C5
A5-M-B4-C5
A8-M-B1-C5
A8-M-B4-C5
A2-M-B1-C5
A2-M-B4-C5
A3-M-B9-C2
A3-M-B10-C2
A4-M-B10-C2
A1-M-B10-C2
A5-M-B10-C2
A3-M-B9-C5
A7-M-B9-C5
A1-M-B9-C5
A1-M-B10-C5
A9-M-B5-C1
A9-M-B7-C1
A9-M-B5-C2
A9-M-B7-C2
A9-M-B5-C3
A9-M-B7-C3
A9-M-B8-C3
A9-M-B5-C4
A9-M-B5-C5
A9-M-B5-C6
A9-M-B7-C6
A9-M-B8-C6
A9-M-B5-C7
A9-M-B6-C7
A9-M-B8-C7
A9-M-B5-C8
A9-M-B7-C8
A9-M-B8-C8
A9-M-B13-C2
A9-M-B13-C5
A9-M-B13-C6
A9-M-B13-C8
A9-M-B1-C1
A9-M-B4-C2
A9-M-B3-C3
A9-M-B1-C4
A9-M-B3-C4
A9-M-B1-C5

-continued

A9-M-B3-C5
A9-M-B4-C5
A9-M-B2-C6
A9-M-B3-C6
A9-M-B4-C6
A9-M-B3-C7
A9-M-B1-C8
A9-M-B2-C8
A9-M-B3-C8
A9-M-B4-C8
A9-M-B9-C1
A9-M-B9-C2
A9-M-B10-C2
A9-M-B11-C2
A9-M-B9-C3
A9-M-B10-C3
A9-M-B11-C3
A9-M-B9-C4
A9-M-B10-C4
A9-M-B11-C4
A9-M-B9-C5
A9-M-B12-C5
A9-M-B10-C5
A9-M-B11-C5
A9-M-B9-C6
A9-M-B12-C6
A9-M-B10-C6
A9-M-B11-C6
A9-M-B9-C7
A9-M-B12-C7
A9-M-B10-C7
A9-M-B11-C7
A9-M-B9-C8
A9-M-B12-C8
A9-M-B10-C8

TABLE I

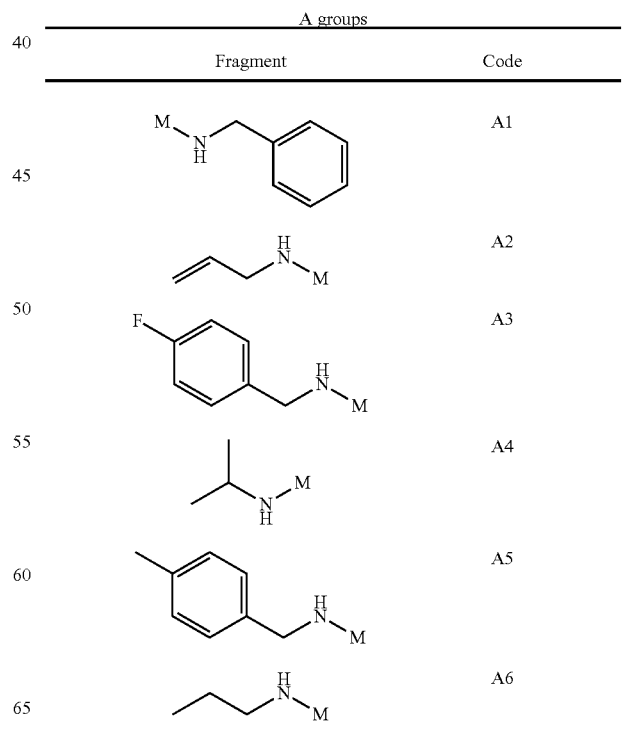

| A groups | |
|---|---|
| Fragment | Code |
|  | A1 |
|  | A2 |
|  | A3 |
|  | A4 |
|  | A5 |
|  | A6 |

TABLE I-continued

A groups

| Fragment | Code |
|---|---|
| (3-methoxybenzyl)amine, M-NH-CH2-C6H4-OCH3 | A7 |
| ethoxyethylamine, CH3CH2-O-CH2CH2-NH-M | A8 |
| H2N-M (hydrazine) | A9 |

TABLE II

B groups

| Fragment | Code |
|---|---|
| methanesulfonyl, CH3-S(=O)2-M | B1 |
| p-toluenesulfonyl | B2 |
| ethanesulfonyl, CH3CH2-S(=O)2-M | B3 |
| benzenesulfonyl, M-S(=O)2-C6H5 | B4 |
| benzoyl, M-C(=O)-C6H5 | B5 |
| acetyl, M-C(=O)-CH3 | B6 |
| p-toluoyl | B7 |
| cyclopropanecarbonyl | B8 |
| propylureido | B9 |
| propylureido (isomer) | B10 |
| benzylcarbamoyl | B11 |
| piperazine-1-carbonyl | B12 |
| H | B13 |
| 4-acetamidobenzenesulfonyl | B14 |
| butylureido | B15 |

TABLE III

C groups

| Fragment | Code |
|---|---|
| cyclopropylmethyl | C1 |
| methyl | C2 |
| ethyl | C3 |
| allyl | C4 |

TABLE III-continued

C groups

| Fragment | Code |
|---|---|
| 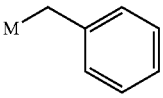 | C5 |
| 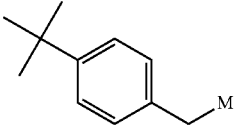 | C6 |
| 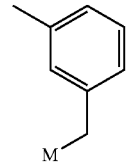 | C7 |
| 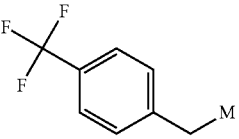 | C8 |
|  | C9. |

11. A pharmaceutical composition comprising a therapeutically effective amount of a compound of formula (I)

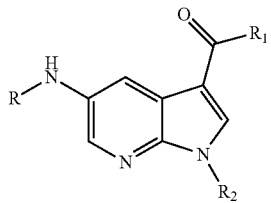

wherein

R is selected from the group consisting of —$R^a$, —$COR^a$, —$CONR^aR^b$, —$SO_2R^a$ and —$COOR^a$;

$R_1$ is —$NR^cR^d$ or —$OR^c$;

wherein $R^a$, $R^b$, $R^c$ and $R^d$ are the same or different and are each independently hydrogen or a group, optionally further substituted, which is straight or branched $C_1$-$C_6$ alkyl, straight or branched $C_2$-$C_6$ alkenyl, straight or branched $C_2$-$C_6$ alkynyl, $C_3$-$C_6$ cycloalkyl, $C_3$-$C_6$ cycloalkyl $C_1$-$C_6$ alkyl, an aryl, aryl $C_1$-$C_6$ alkyl, a heterocycle and heterocycle $C_1$-$C_6$ alkyl or, taken together with the nitrogen atom to which they are bonded, $R^a$ and $R^b$ as well as $R^c$ and $R^d$ form a 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine or azetidine group;

$R_2$ is a group, optionally further substituted, selected from the group consisting of straight or branched $C_1$-$C_6$ alkyl, straight or branched $C_2$-$C_6$ alkenyl, straight or branched $C_2$-$C_6$ alkynyl, $C_3$-$C_6$ cycloalkyl, $C_3$-$C_6$ cycloalkyl $C_1$-$C_6$ alkyl, aryl, aryl $C_1$-$C_6$ alkyl, heterocycle and heterocycle $C_1$-$C_6$ alkyl;

wherein any of $R^a$, $R^b$, $R^c$, $R^d$ or $R_2$ is independently optionally substituted by halogen, nitro, oxo groups, carboxy, cyano, alkyl, perfluoroalkyl, alkenyl, cycloalkyl, cycloalkenyl, aryl, heterocyclyl, amino groups, carbonylamino groups, hydroxy groups, carbonyl groups or sulfurated groups;

wherein said aryl is selected from the group consisting of phenyl, indanyl, biphenyl, α- or β-naphthyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, quinolinyl, isoquinolinyl, quinoxalinyl, benzofurazanyl, 1,2,3-triazolyl and 1-phenyl-1,2,3-triazolyl;

wherein said heterocycle is selected from the group consisting of 1,3-dioxolane, pyran, pyrrolidine, pyrroline, imadazoline, imidazolidine, pyrazolidine, pyrazoline, piperidine, piperazine, morpholine, tetrahydrofuran, hexamethyleneimine, 1,4-hexahydrodiazepine and azetidine;

or isomers, tautomers, and pharmaceutically acceptable salts thereof and, at least, one pharmaceutically acceptable excipient, carrier and/or diluent.

12. The pharmaceutical composition according to claim 11 further comprising one or more chemotherapeutic agents.

13. A kit comprising a compound of formula (I)

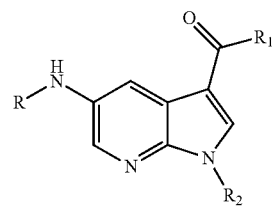

wherein

R is selected from the group consisting of —$R^a$, —$COR^a$, —$CONR^aR^b$, —$SO_2R^a$ and —$COOR^a$;

$R_1$ is —$NR^cR^d$ or —$OR^c$;

wherein $R^a$, $R^b$, $R^c$ and $R^d$ are the same or different and are each independently hydrogen or a group, optionally further substituted, which is straight or branched $C_1$-$C_6$ alkyl, straight or branched $C_2$-$C_6$ alkenyl, straight or branched $C_2$-$C_6$ alkynyl, $C_3$-$C_6$ cycloalkyl, $C_3$-$C_6$ cycloalkyl $C_1$-$C_6$ alkyl, an aryl, aryl $C_1$-$C_6$ alkyl, a heterocycle and heterocycle $C_1$-$C_6$ alkyl or, taken together with the nitrogen atom to which they are bonded, $R^a$ and $R^b$ as well as $R^c$ and $R^d$ form a 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine or azetidine group;

$R_2$ is a group, optionally further substituted, selected from the group consisting of straight or branched $C_1$-$C_6$ alkyl, straight or branched $C_2$-$C_6$ alkenyl, straight or branched $C_2$-$C_6$ alkynyl, $C_3$-$C_6$ cycloalkyl, $C_3$-$C_6$ cycloalkyl $C_1$-$C_6$ alkyl, aryl, aryl $C_1$-$C_6$ alkyl, heterocycle and heterocycle $C_1$-$C_6$ alkyl;

wherein any of $R^a$, $R^b$, $R^c$, $R^d$ or $R_2$ is independently optionally substituted by halogen, nitro, oxo groups, carboxy, cyano, alkyl, perfluoroalkyl, alkenyl, cycloalkyl, cycloalkenyl, aryl, heterocyclyl, amino groups, carbonylamino groups, hydroxy groups, carbonyl groups or sulfurated groups;

wherein said aryl is selected from the group consisting of phenyl, indanyl, biphenyl, α- or β-naphthyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, quinolinyl, isoquinolinyl, quinoxalinyl, benzofurazanyl, 1,2,3-triazolyl and 1-phenyl-1,2,3-triazolyl;

wherein said heterocycle is selected from the group consisting of 1,3-dioxolane, pyran, pyrrolidine, pyrroline, imadazoline, imidazolidine, pyrazolidine, pyrazoline, piperidine, piperazine, morpholine, tetrahydrofuran, hexamethyleneimine, 1,4-hexahydrodiazepine and azetidine;

or isomers, tautomers, and pharmaceutically acceptable salts thereof and, at least optionally associated with a pharmaceutical excipient or carrier and/or diluent, and one or more chemotherapeutic agents.

14. A method for inhibiting one or more protein kinases selected from the group consisting of cdk2, cdk5, protein kinase C, PAK-4, PAK-5, ZC-1, STLK-2, DDR-2, Aurora 1, Aurora 2, Bub 1, PLK, Chk1, Chk2, HER2, raf1, MEK1, MAPK, EGF-R, PDGF-R, FGF-R, PI3K, week kinase, Src, Abl, ILK, MK-2, IKK-2, Cdc7 which comprises contacting said kinase with an effective amount of a pyrrolo[2,3-b]pyridine represented by formula (I)

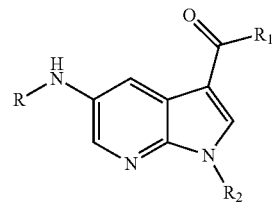

(I)

wherein

R is —$R^a$, —$COR^a$, —$CONR^aR^b$, —$SO_2R^a$ or —$COOR^a$;

$R_1$ is —$NR^cR^d$ or —$OR^c$;

wherein $R^a$, $R^b$, $R^c$ and $R^d$, are the same or different, and are each independently hydrogen or a group optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl or, taken together with the nitrogen atom to which they are bonded, $R^a$ and $R^b$ as well as $R^c$ and $R^d$, may form a 1,3-dioxolane, pyran, pyrrolidine, pyrroline, imidazoline, imidazolidine, pyrazolidine, pyrazoline, piperidine, piperazine, morpholine, tetrahydrofuran, hexamethylenediamine, 1,4-hexahydrodiazepine or azetidine group;

$R_2$ is a group, optionally further substituted, selected from straight or branched $C_1$-$C_6$ alkyl, straight or branched $C_2$-$C_6$ alkenyl, straight or branched $C_2$-$C_6$ alkynyl, $C_3$-$C_6$ cycloalkyl or cycloalkyl $C_1$-$C_6$ alkyl, aryl or aryl $C_1$-$C_6$ alkyl, or heterocycle or heterocycle $C_1$-$C_6$ alkyl;

or isomers, tautomers, and pharmaceutically acceptable salts thereof.

\* \* \* \* \*